United States Patent
Van Benthem et al.

(10) Patent No.: US 10,551,247 B1
(45) Date of Patent: Feb. 4, 2020

(54) GLOBAL ANALYSIS PEAK FITTING FOR CHEMICAL SPECTROSCOPY DATA

(71) Applicant: National Technology & Engineering Solutions of Sandia, LLC, Albuquerque, NM (US)

(72) Inventors: Mark Van Benthem, Albuquerque, NM (US); James A. Ohlhausen, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 81 days.

(21) Appl. No.: 15/082,922

(22) Filed: Mar. 28, 2016

Related U.S. Application Data

(60) Provisional application No. 62/153,303, filed on Apr. 27, 2015.

(51) Int. Cl.
| | | |
|---|---|---|
| *G01J 3/42* | (2006.01) | |
| *G01N 21/31* | (2006.01) | |
| *G01N 21/64* | (2006.01) | |
| *G01N 23/083* | (2018.01) | |

(52) U.S. Cl.
CPC ............... *G01J 3/42* (2013.01); *G01N 21/31* (2013.01); *G01N 21/64* (2013.01); *G01N 23/083* (2013.01)

(58) Field of Classification Search
CPC .................................. G01J 3/42; G01N 21/31
See application file for complete search history.

(56) References Cited

U.S. PATENT DOCUMENTS

| | | | |
|---|---|---|---|
| 6,584,413 B1 | 6/2003 | Keenan et al. | |
| 6,675,106 B1 | 1/2004 | Keenan et al. | |
| 6,922,645 B2 | 7/2005 | Haaland et al. | |
| 7,283,684 B1 | 10/2007 | Keenan | |
| 7,400,772 B1 | 7/2008 | Keenan | |
| 7,451,173 B1 | 11/2008 | Van Benthem et al. | |
| 7,472,153 B1 | 12/2008 | Keenan | |
| 7,491,944 B1 | 2/2009 | Stork et al. | |
| 7,725,517 B1 | 5/2010 | Keenan | |
| 7,840,626 B1 | 11/2010 | Keenan | |
| 8,266,197 B1 | 9/2012 | Van Benthem et al. | |
| 8,761,450 B2 | 6/2014 | Hill et al. | |
| 2005/0221514 A1* | 10/2005 | Pasadyn ................ | G05B 11/42 438/14 |
| 2010/0276578 A1* | 11/2010 | Shelley .............. | G01N 21/3563 250/252.1 |

(Continued)

OTHER PUBLICATIONS

Andrew JJ et al., "Rapid analysis of Raman image data using two-way multivariate curve resolution," *Appl. Spectrosc.* 1998;52(6):797-807.

(Continued)

*Primary Examiner* — Michele Fan
(74) *Attorney, Agent, or Firm* — Helen S. Baca

(57) ABSTRACT

The present invention relates to methods for analyzing a chemical sample. For instance, the methods herein allow for global analysis of spectroscopy data in order to extract useful chemical properties from complicated multidimensional data. Such analysis can optionally employ data compression to further expedite computer-implemented computation. In particular, the methods herein provide global analysis of data matrices explained by both linear and non-linear terms.

26 Claims, 23 Drawing Sheets

(56) References Cited

U.S. PATENT DOCUMENTS

| | | | | |
|---|---|---|---|---|
| 2011/0284639 A1* | 11/2011 | Lee | ............................ | C40B 20/04 |
| | | | | 235/468 |
| 2013/0196445 A1* | 8/2013 | Kinoshiro | ............ | G01N 21/643 |
| | | | | 436/123 |
| 2015/0092921 A1* | 4/2015 | Hansford | ............. | G01N 23/223 |
| | | | | 378/76 |

OTHER PUBLICATIONS

Beechem JM, "Global analysis of biochemical and biophysical data," *Methods Enzymol.* 1992;210:37-54.

Culter PJ et al., "Methods for kinetic modeling of temporally resolved hyperspectral confocal fluorescence images," *Appl. Spectrosc.* 2009;63(2):153-63.

Cutler PJ et al., "Systematic method for the kinetic modeling of temporally resolved hyperspectral microscope images of fluorescently labeled cells," *Appl. Spectrosc.* 2009;63(3):261-70.

Dhez O et al., "Calibrated NEXAFS spectra of some common polymers," *J. Electron Spectrosc. Relat. Phenom.* 2003;128(1):85-96.

Dvorak MA et al., "On-the-fly fluorescence lifetime determination with total emission detection with HPLC," *Anal. Chem.* 1997;69:3458-64.

Gamble LJ et al., "Surface structure and orientation of PTFE films determined by experimental and FEFF8-calculated NEXAFS spectra," *Langmuir* 2002;18:2183-9.

Haaland DM et al., "Application of new least-squares methods for the quantitative infrared analysis of multicomponent samples," *Appl. Spectrosc.* 1982;36(6):665-73.

Hähner G, "Near edge X-ray absorption fine structure spectroscopy as a tool to probe electronic and structural properties of thin organic films and liquids," *Chem. Soc. Rev.* 2006;35:1244-55.

Hemraj-Benny T et al., "Near-edge X-ray absorption fine structure spectroscopy as a tool for investigating nanomaterials," *Small* 2006;2(1):26-35.

Keenan MR et al., "Accounting for Poisson noise in multivariate analysis of ToF-SIMS spectrum images," *Surf. Interface Anal.* 2004;36:203-12.

Keenan MR et al., "Algorithms for constrained linear unmixing with application to the hyperspectral analysis of fluorophore mixtures," *Proc. SPIE* 2002;4186:193-202.

Keenan MR, "Exploiting spatial-domain simplicity in spectral image analysis," *Surf. Interface Anal.* 2008;41:79-87.

Keenan MR, "Multivariate analysis of spectral images composed of count data," in *Techniques and Applications of Hyperspectral Image Analysis* (eds. H.F. Grahn and P. Geladi), John Wiley & Sons, Hoboken, NJ, 2007, pp. 89-126, chp. 5.

Knorr FJ et al., "Resolution of multicomponent fluorescence spectra by an emission wavelength-decay time data matrix," *Anal. Chem.* 1981;53:272-6.

Knutson JR et al., "Simultaneous analysis of multiple fluorescence decay curves: a global approach," *Chem. Phys. Lett.* 1983;102(6):501-7.

Kotula PG et al., "Tomographic spectral imaging with multivariate statistical analysis: comprehensive 3D microanalysis," *Microsc. Microanal.* 2006;12:36-48.

Outka DA et al., "Curve fitting analysis of near-edge core excitation spectra of free, adsorbed, and polymeric molecules," *J. Chem. Phys.* 1988;88:3539-54.

Penner-Hahn JE, "X-ray absorption spectroscopy," in *Comprehensive Coordination Chemistry*, vol. II (eds.-in-chief J.A. McCleverty and T.J. Meyer; vol. ed. A.B.P. Lever), Elsevier Ltd., Amsterdam, Netherlands, 2003, pp. 159-86, chp. 2.13.

Van Benthem MH et al., "Fast algorithm for the solution of large-scale non-negativity-constrained least squares problem," *J. Chemom.* 2004;18:441-50.

Van Benthem MH et al., "Global analysis peak fitting for imaging NEXAFS data," *36th Annual Symposium on Applied Surface Analysis*, held on Jun. 2-5, 2014 in Albuquerque, NM (19 pp.).

Van Benthem MH et al., "Global analysis peak fitting applied to EELS images," *Microsc. Microanal.* 2015;21(Suppl. 3):1421-2.

Varmuza K et al., "Principal component analysis," in *Introduction to Multivariate Statistical Analysis in Chemometrics*, CRC Press, Boca Raton, FL, 2009, pp. 59-102, chp. 3.

Wold S et al., "PLS-regression: a basic tool of chemometrics," *Chemom. Intell. Lab. Sys.* 2001;58:109-30.

Wold S et al., "Principal component analysis," *Chemom. Intell. Lab. Sys.* 1987;2:37-52.

Wu W et al., "The kernel PCA algorithms for wide data. Part I: theory and algorithms," *Chemom. Intell. Lab. Sys.* 1997;36:165-72.

Zhou PH et al., "Electronic structure of photo-degraded polypropylene ultrathin films," *Chem. Phys. Lett.* 2008;465(4-6):241-4.

\* cited by examiner

Analytical model: $D = AS^T$ $I_G = Ae^{-\left(\frac{E-E_0}{w}c\right)^2}$;
where $c = 2\sqrt{\log 4}$ $I_S = A\left[\frac{1}{2} + \frac{1}{2}\mathrm{erf}\left(\frac{E-E_0}{w}d\right)\right]$;
where $d = 2\sqrt{\log 2}$ Application of least squares criterion

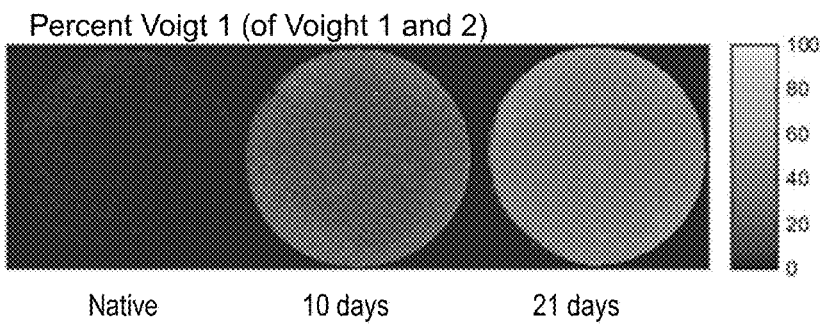
FIG. 14A
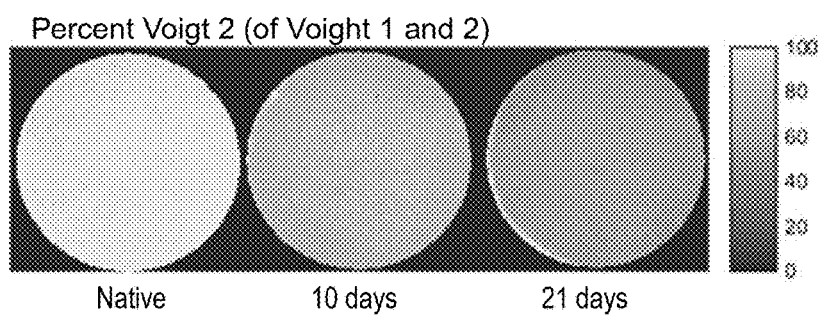
FIG. 14B
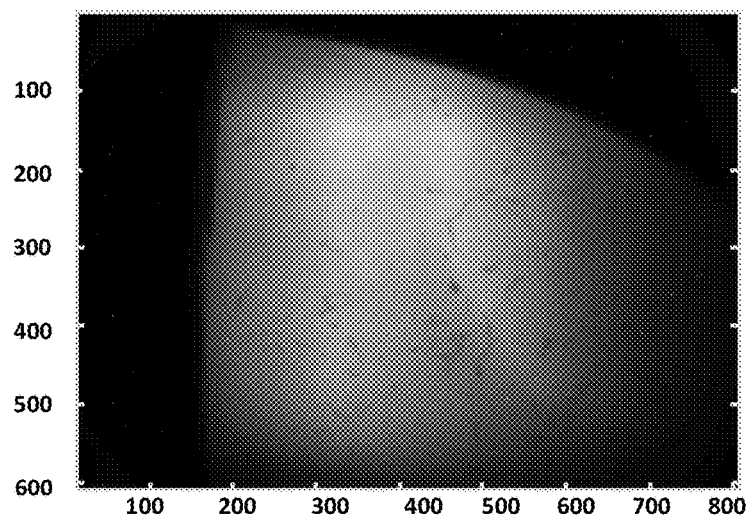
FIG. 15A
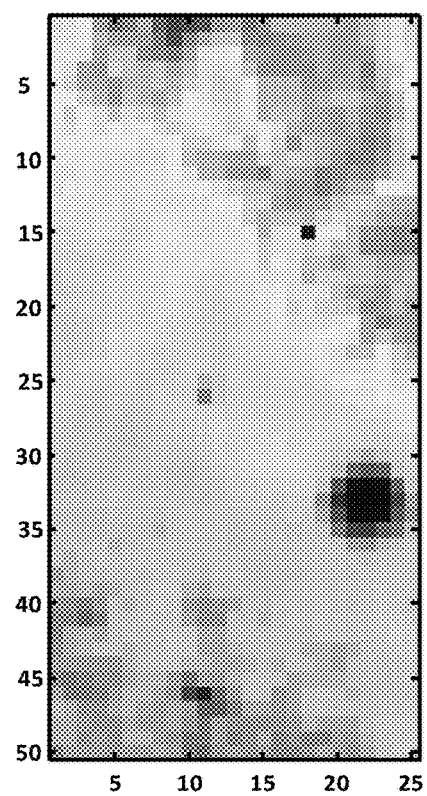

GLOBAL ANALYSIS PEAK FITTING FOR CHEMICAL SPECTROSCOPY DATA

CROSS-REFERENCE TO RELATED APPLICATION

This application claims the benefit of U.S. Provisional Application No. 62/153,303, filed Apr. 27, 2015, which is hereby incorporated by reference in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

REFERENCE TO A COMPUTER PROGRAM LISTING APPENDIX

A computer program listing appendix including an ASCII formatted file accompanies this application. The appendix includes a file named "SD_13122_0_Global_NEXAFS.txt," created on Apr. 13, 2015 (size of 14.3 kilobytes), which is hereby incorporated by reference in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to methods for analyzing a chemical sample. For instance, the methods herein allow for global analysis of complicated multidimensional data in order to extract useful chemical properties. Such analysis can optionally employ data compression to further expedite computation.

BACKGROUND OF THE INVENTION

Modern spectroscopy techniques can yield data including spectral image information in multiple spatial, temporal, and other experimental dimensions. Exemplary data can include tens of thousands of images or spectra for a single chemical sample. Understanding the chemical or physical phenomenon underlying such data can be challenging. Thus, a remaining challenge is the ability to reduce vast quantities of data into meaningful chemical information, such as the presence or absence of particular chemical bonds, atoms, charge, etc., while maintaining important dimensional information.

Various methods simplify the analysis but have limitations. For instance, one technique to simplify data is to analyze a single mean spectrum (e.g., a mean spectrum that includes a mean average of intensity data for over 10,000 spectra). This technique reduces the data into a single spectrum but at the cost of removing other valuable information, such as spatial locations of a particular chemical species, time-dependent changes of a concentration of a particular chemical species, etc. In another instance, complex chemical interactions are conventionally modeled and solved in a linear manner. This simplification may incorrectly explain such interactions, as many chemical reactions are best explained (in whole or in part) by non-linear mechanisms. Accordingly, additional methods are desired that facilitate expeditious analysis of complicated data while maintaining the data set and/or accommodating non-linear phenomenon.

SUMMARY OF THE INVENTION

The present invention relates to methods for global analysis of chemical spectroscopy data. In particular, we show that this method is effective for analyzing spectral image data to extract information about chemical bonds in a chemical test sample. Spectral image data typically include numerous images that record emission signals from a test sample after irradiation (e.g., with an X-ray source). The method can fit recorded emission signals to peaks described by non-linear functions. Proposed fits are refined by combining non-linear and linear optimization techniques. It takes advantage of the high dimensionality of the image space to yield peaks with potentially greater reliability than single spectrum fitting. In this way, the methods employ global analysis, i.e., simultaneous analysis of the entire data set in all dimensions. In some embodiments, the method employs data compression with principal component analysis (PCA) to rapidly complete the analysis.

In one aspect, the invention features a method (e.g. a computer-implemented method) for analyzing a chemical test sample (e.g., any herein), the method including: receiving (e.g., with a processor) an image array of the chemical test sample, where the array includes $d_n$ number of images for each $n^{th}$ energy level, where each image includes dimensions of a by b (e.g., and optionally c, such as dimensions a by b by c), and where each of $d_n$, n, a, b, and c, if present, is, independently, an integer of 1 or more; generating (e.g., with a processor) a data matrix D based on the image array, where D has a dimension of m by n, and where m includes a times b (or m includes a times b times c); performing (e.g., with a processor) global analysis of D, thereby generating a matrix A including linear terms and a matrix S including non-linear terms, where $D=AS^T$, A has a dimension of m by q, S has a dimension of n by q, and q is an integer of 1 or more that represents a number of factors; and converting the matrix A and the matrix S (e.g., into one or more chemical spectra or one or more absorption images that characterizes the chemical test sample).

In some embodiments, the performing step (e.g., for global analysis) includes solving for an estimated matrix $\hat{S}$ by non-linearly solving $D=AS^T$, where the estimated matrix $\hat{S}$ is an estimate of S; solving for an estimated matrix $\hat{A}$ using the estimated matrix $\hat{S}$ as S in the following equation $D=AS^T$, where the estimated matrix $\hat{A}$ is an estimate of A; computing a convergence metric; and iterating these recited steps (e.g., for an i number of iterations, where i is an integer of 1 or more) until the convergence metric meets a convergence criterion. In other embodiments, the estimated matrix $\hat{S}$ is a matrix $\hat{S}_i$, which is an $i^{th}$ estimate of S. In yet other embodiments, the estimated matrix $\hat{A}$ is a matrix $\hat{A}_i$, which is an $i^{th}$ estimate of A.

In some embodiments, the performing step (e.g., for global analysis) includes constructing an initial matrix $\hat{S}_{initial}$ composed of expected non-linear terms. In other embodiment, the performing step includes solving for an estimated matrix $\hat{S}$ by non-linearly solving $D=AS^T$ by beginning from the initial matrix $\hat{S}_{initial}$. In yet other embodiment, the performing step includes solving for an estimated matrix $\hat{A}$ using $\hat{S}$ as S in the following equation $D=AS^T$, where the estimated matrix $\hat{A}$ is an estimate of A; computing a convergence metric; and iterating these recited steps until convergence (e.g., the convergence metric meets a convergence criterion). In some embodiments, the performing step further includes, if not converged, solving for an estimated matrix $\hat{S}$ by non-linearly solving $D=AS^T$.

In some embodiments, the method further includes compressing the data matrix D to provide a score matrix T and a loading matrix P, where $D=TP^T$ (e.g., where the compressing step is conducted prior to the step of performing global analysis).

In further embodiments, the method includes performing (e.g., with a processor) global analysis of compressed D, thereby generating a matrix A and a matrix S (e.g., as described herein, and optionally where $D=TP^T=AS^T$).

In another aspect, the invention features a method (e.g., a computer-implemented method) for analyzing a chemical test sample (e.g., any herein), the method including: receiving (e.g., with a processor) an image array of the chemical test sample, where the array includes $d_n$ number of images for each $n^{th}$ energy level, and where each image includes dimensions of a by b (e.g., and optionally c, such as dimensions a by b by c), and where each of $d_n$, n, a, b, and c, if present, is, independently, an integer of 1 or more; generating, with a processor, a data matrix D based on the image array, where D has a dimension of m by n, and where m is a times b (or m includes a times b times c); compressing the data matrix D to provide a score matrix T and a loading matrix P, where $D=TP^T$; performing (e.g., with a processor) global analysis of D, thereby generating a matrix A including linear terms and a matrix S including non-linear terms, where $D=TP^T=AS^T$ (e.g., where A has a dimension of m by q, S has a dimension of n by q, and q is an integer of 1 or more that represents a number of factors); and converting the matrix A and the matrix S (e.g., into one or more chemical spectra or one or more absorption images that characterizes the chemical test sample).

In some embodiments, the compressing step includes an eigenanalysis of $D=TP^T$ (e.g., as described herein, such as by Eq. 12).

In other embodiments, the compressing step includes solving for the loading matrix P by analysis of $D=TP^T$ (e.g., as described herein, such as by Eqs. 12, 15a, 15b, or 15c).

In yet other embodiments, the compressing step includes solving for the loading matrix P by analysis of $D=TP^T$; and solving for the score matrix T by using the loading matrix P (e.g., as described herein, such as by Eqs. 13 or 15b).

In some embodiments, D is an m×n matrix, T is an m×p matrix, and $P^T$ is an p×n matrix; each of m, n, and p is an integer of 1 or more. In further embodiments, p is less than both m and n.

In some embodiments, the performing step (e.g., for global analysis) includes solving for an estimated matrix $\hat{S}$ by non-linearly solving $D=AS^T$, where the estimated matrix $\hat{S}$ is an estimate of S; solving for an estimated matrix $\hat{A}$ using the estimated matrix $\hat{S}$ as S in the following equation $AS^T=TP^T$ (e.g., by using Eqs. 17, 19, or 20), where the estimated matrix $\hat{A}$ is an estimate of A; computing a convergence metric; and iterating these recited steps (e.g., for an i number of iterations, where i is an integer of 1 or more) until the convergence metric meets a convergence criterion. In other embodiments, the estimated matrix $\hat{S}$ is a matrix $\hat{S}_i$, which is an $i^{th}$ estimate of S. In yet other embodiments, the estimated matrix $\hat{A}$ is a matrix $\hat{A}_i$, which is an $i^{th}$ estimate of $\hat{A}$.

In some embodiments, the performing step (e.g., for global analysis) includes solving for an estimated matrix $\hat{S}$ by non-linearly solving $D=AS^T$, where the estimated matrix $\hat{S}$ is an estimate of S; solving for an estimator matrix $\tilde{A}$ using $\hat{S}$ as S in the following equation $P^T=\tilde{A}S^T$ (e.g., by using Eqs. 17, 18, 19, or 20), where the estimator matrix $\hat{A}$ is an estimator of A such that $A=T\tilde{A}$; computing a convergence metric; and iterating these recited steps (e.g., for an i number of iterations, where i is an integer of 1 or more) until the convergence metric meets a convergence criterion. In other embodiments, the estimated matrix $\hat{S}$ is a matrix $\hat{S}_i$, which is an $i^{th}$ estimate of S. In yet other embodiments, the estimator matrix $\tilde{A}$ is a matrix $\tilde{A}_i$, which is an $i^{th}$ estimator of A. In some embodiment, the performing step further includes computing the matrix A by using the estimator matrix $\tilde{A}$ in the following equation $A=T\tilde{A}$, where $T=DP$.

In any embodiments herein, the performing step (e.g., for global analysis) includes computing a residual matrix R (e.g., as described herein) that characterizes error between D and one or more generated matrices (e.g., matrices A, $A_i$, $\hat{A}$, $\tilde{A}$, $\hat{A}_{initial}$, S, $\hat{S}_{initial}$, $\hat{S}_i$, T, P, $\hat{D}$, or any described herein).

In any embodiment herein, the performing step includes performing (e.g., with a processor) global analysis of D, thereby generating an $i^{th}$ matrix $A_i$ (e.g., a first matrix $A_1$) including linear terms and an $i^{th}$ matrix $S_i$ (e.g., a first matrix $S_1$) including non-linear terms; computing an $i^{th}$ matrix $R_i$ (e.g., a first residual $R_1$) that characterizes error between D and generated matrix $A_i$ and matrix $S_i$; iterating these recited steps (e.g., for an i number of iterations, where i is an integer of 1 or more) until convergence to provide matrix A and matrix S for further analysis (e.g., for the converting step, such as any described herein).

In any embodiments herein, the performing step (e.g., for global analysis) includes a non-negativity constraint or an equality constraint.

In any embodiment herein, the performing step (e.g., for global analysis) includes applying a least squares minimization criterion to generate the matrices A, S, or any other useful matrix (e.g., as described herein).

In any embodiment herein, the convergence metric includes a residual matrix R.

In any embodiment herein, the method includes computing the residual matrix R and employing matrix R in any useful manner. In one instance, matrix R is computed and then a sum squared residual (SSR) is computed based on matrix R. In a further instance, the SSR is passed to an optimization function, which in turn computes a further estimated matrix $\hat{S}$ having improved non-linear terms (e.g., as determined by computing a gradient in the change of the non-linear terms). Then, further estimated matrix $\hat{A}$ can be computed (e.g., by applying least squares), and an even further estimated matrix $\hat{S}$ can be computed (e.g., by applying the Levenberg-Marquardt method, the Gauss-Newton method, the gradient descent method, other downhill methods, etc.). In any embodiment herein, steps can be iterated until the residual matrix R meets a convergence criterion.

In any embodiment herein, one or more factors are selected from the group consisting of a Gaussian function, a Lorentzian function, a pseudo-Voigt function, an asymmetric peak function, a shaped step function, and an offset function In any embodiment herein, the image array includes one or more absorption images or spectra of the chemical test sample (e.g., a polymer, a monomer, a film, an organic film, a metal, a molecular complex, a gas, or a liquid). Exemplary, non-limiting absorption images or spectra include one or more X-ray absorption spectra, near edge X-ray absorption fine structure spectra, fluorescence spectra, infrared spectra, photon emission spectra, or photon absorption spectra, or any other images or spectra described herein.

Definitions

As used herein, the term "spectrum" or "spectra" is broadly defined to also include an "energy spectrum" (e.g., for x-ray absorption spectroscopy), a "mass spectrum" (for mass spectroscopy), a "wavelength spectrum" (e.g., for wavelength dispersive analysis, WDS), a "frequency spectrum" (e.g., for Fast Fourier Transform analysis), or an "acoustic spectrum" (e.g., for sound/speech analysis), as well as an image representing any of these spectra. A spectrum can be created, e.g., by detecting radiation (e.g., photons or particles) emitted within a specified interval (window) of energy (e.g., mass, wavelength, or frequency) and as a function of energy (e.g., mass, wavelength, or frequency).

The term "radiation emitted by a test sample" is broadly defined to include any type of photon or particle, including, but not limited to: radio waves, sound waves, microwaves, visible light, infrared radiation, ultraviolet radiation, X-rays, gamma-rays, electrons, positrons, protons, neutrons, neutral particles, alpha particles, charged particles (ions), ionized atoms, ionized molecules, and/or excited molecules. Emission can include any radiation emitted from the sample, including the transmission of radiation through a sample, either completely or partially, which is subsequently "emitted" from the far side of the sample; scattering or reflection of particles from a surface; and/or sputtering processes (e.g., as in secondary ion mass spectroscopy).

As used herein, the term "about" means +/−10% of any recited value. As used herein, this term modifies any recited value, range of values, or endpoints of one or more ranges.

Other features and advantages of the invention will be apparent from the following description and the claims.

BRIEF DESCRIPTION OF THE DRAWINGS

FIG. 14A-14B shows a comparison of the presence of either factor 1 or 2 in the native nitrile sample, the aged sample (10 days), and another aged sample (21 days). Provided are a reconstructed image showing the percentage of the factor 1 (the first Voigt fit), as compared to the total presence of the sum of factors 1 and 2 (FIG. 14A); and a reconstructed image showing the percentage of the factor 2 (the second Voigt fit), as compared to the total presence of the sum of factors 1 and 2 (FIG. 14B).

FIG. 15A-15B shows NEXAFS images and spectrum of a sample containing polytetrafluoroethylene (PTFE). Provided are spectrally summed NEXAFS images of the entire region (600 pixels by 800 pixels, left, FIG. 15A) and an region of interest (ROI) having dimensions of 50 pixels by 25 pixels (right, FIG. 15A). Also provided is a mean spectrum obtained from NEXAFS images (FIG. 15B).

DETAILED DESCRIPTION OF THE INVENTION

Figure 1A:
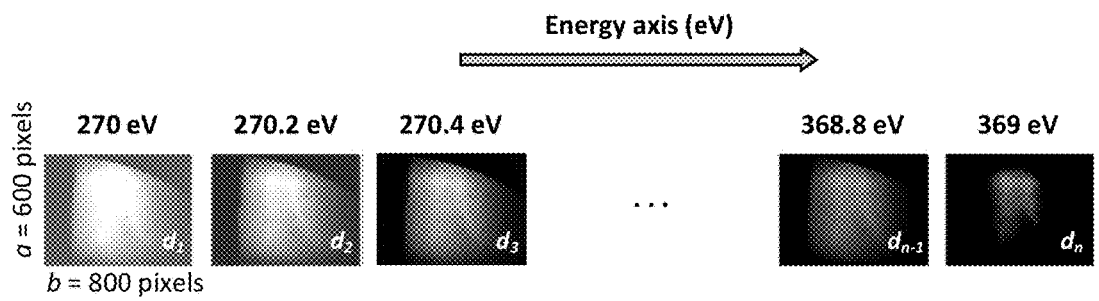
FIG. 1A-1D shows schematics of data matrix D represented in different ways. Provided are an image array including a plurality of individual images (labeled $d_1$, $d_2$, ..., $d_{n-1}$, $d_n$), in which each image is obtained at a discrete $n^{th}$ energy level (FIG. 1A); a data matrix D composed of an m×n matrix, in which m is the number of pixels for each $d_n$ image and n is the number of energy levels (FIG. 1B); a representation of matrix D collapsed along the spectral dimension (FIG. 1C); and a representation of matrix D collapsed along the image dimension (FIG. 1D).

The present invention relates to global analysis of multidimensional data. In general, global analysis includes simultaneous analysis of all measurements provided in a data set (e.g., a data matrix D). Global analysis is different from analytical techniques in which an averaged image or spectrum is analyzed or in which an individual image or spectrum is analyzed one at a time (i.e., sequential analysis). Taking the example for NEXAFS analysis, conventional analytical techniques generally do not employ an entire, multidimensional data set. Instead, an average spectrum profile is generated by summing the intensity observed in an image for a particular photon energy level, thereby generating a profile having two dimensions: intensity and photon energy. Using this two-dimensional profile, the various peaks can be fit using minimal computation time and without employing global analysis.

In contrast, global analysis requires simultaneous analysis of the entire data set in all dimensions, e.g., multiple (more than two) dimensions providing spatial information and spectral information. Due to the large amount of data, global analysis can be challenging. In addition, many chemical phenomena are more appropriately characterized by non-linear functions, but many curve analysis techniques require or impose linear constraints to facilitate analysis by matrix decomposition methodologies (e.g., principal component analysis). Thus, the present invention encompasses a method of analyzing multidimensional data for chemical test samples by fitting both non-linear and linear terms. In particular embodiments, the method fits emission bands (from chemical bonds or orbitals) to peaks described by non-linear functions using non-linear and linear optimization techniques. By maintaining the high dimensionality of the image space, the methods herein yield peaks with potentially greater reliability than single spectrum fitting. The methods herein can optionally employ data compression with principal component analysis to rapidly complete the analysis. Additional details follow, which describe how data matrices are generated and then analyzed to provide meaningful chemical information.

Data Matrix and Image Arrays

The present invention employs a data matrix to represent information from a multidimensional image array, which in turn is obtained by detecting radiation emitted by a test sample (e.g., a chemical sample). Many spectroscopy techniques apply energy to a test sample and then detect any resultant radiation emitted by the test sample. The type and intensity of the radiation can be detected and recorded in any useful manner. In particular, such detection can include spatial information, such as the type and intensity of radiation emitted from a particular surface region or volume region from the test sample. Furthermore, a range of energy levels can be applied. Thus, detection can proceed in an energy level-dependent manner, in which one or more radiation measurements are recorded at each energy level. The result is typically an array of spectral data (e.g., images, spectra, etc.) including information on multiple dimensions, such as spectral (e.g., a chemical parameter, such as concentration and identity of each chemical species), experimental (e.g., an energy level or an incidence angle of the radiation source as compared to the molecular axis of a chemical structure in the sample), temporal (e.g., time-dependent changes in a chemical attribute or parameter), and/or spatial (e.g., x-, y-, and/or z-dimensional image of a chemical sample) dimensions.

In one non-limiting example, the image array is obtained from a near edge absorption X-ray fine structure (NEXAFS) spectroscopy experiment. NEXAFS employs an X-ray radiation source to irradiate a test sample at discrete energy levels and a detector to detect radiation emitted from the sample. In one instance, the raw (i.e., measured) data output by NEXAFS (in the form of electrical signals representing X-ray counts or counts per second/minute) is digitized and sorted into "bins," where each bin generally contains four parameters: (1) energy channel number n (i.e., X-ray or photon energy level), (2) X-coordinate of the pixel, (3) Y-coordinate of the pixel, and (4) total number of counts (or intensity). NEXAFS can organize and store the measured data in digital memory in a variety of 2-D or 3-D formats, for example, by channel number, by pixels row-wise, by pixels column-wise, or by other types of channel interleaving.

FIG. 1A shows an exemplary NEXAFS image array, which includes a plurality of images (labeled $d_1$, $d_2$, ... $d_n$). Each image has a dimension of a by b, generally measured in pixels and can be determined by the size of the detector. In addition, each image is obtained at a particular energy level n (e.g., image $d_1$ at energy level $n_1$=270 eV, image $d_2$ at energy level $n_2$=270.0 eV, ... image $d_{496}$ at energy level $n_{496}$=369 eV, in FIG. 1A). In this way, an array is generated having a d number of images at each $n^{th}$ energy level. In some embodiments, one image is obtained at each $n^{th}$ energy level (i.e., d is 1, such that the array has an n number of total images). In other embodiments, a plurality of images is obtained at each $n^{th}$ energy level (e.g., d is 2, 3, 4, 5, 6, 8, 10, etc., such that an array has an n times d number of images).

Image arrays can include any useful d number of images obtained at any useful $n^{th}$ energy level. For instance, a chemical test sample can be irradiated with energy at an $n^{th}$ level, and an image is obtained at each $n^{th}$ level. The number n can be any useful integer (e.g., one or more), and the absolute energy level can be determined by the type of chemical information desired by a user. In some embodiments, the energy levels correspond to X-ray energy levels (e.g., an energy level less than about 2,000 eV). In other embodiments, images and arrays are obtained for chemical test samples treated with X-ray absorption energy levels that result in electronic signatures about 50 eV to about 100 eV above the absorption edge (e.g., above the K-shell edge or above the deepest core shell ionization energy of electrons, such as the ionization energy of 1s electrons).

Figure 1B:
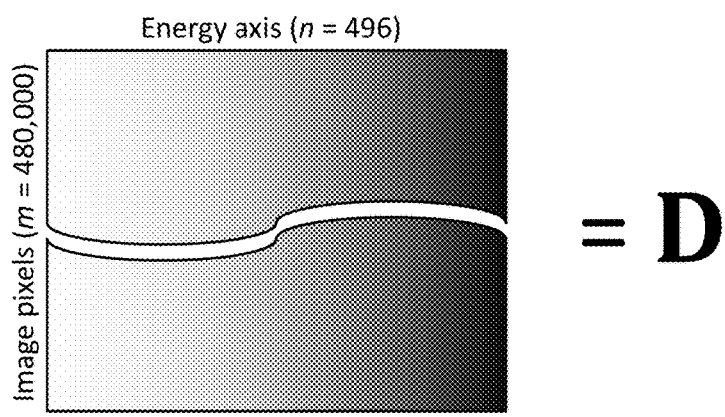
Figure 1C:
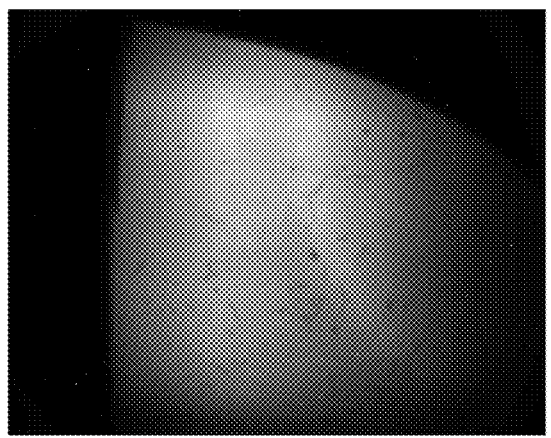

Information from the image array can be used to generate a numerical format that facilitates computation. For instance, such information can be arranged into a data matrix that can be stored, manipulated, inputted, and outputted by a computer processor. Information from a NEXAFS image array can be unfolded into a two-dimensional m×n matrix D, where m is the number of image pixels and n is the number of energy levels. If an entire image is to be analyzed, then m is the number of pixels in the entire image. For instance, for a two-dimensional image having dimensions a by b pixels, m is defined as a times b. As seen in FIG. 1B, data matrix D is an m×n matrix, where m is 480,000 pixels (i.e., a=600 pixels, b=800 pixels, and m=a×b=480,000 pixels) and n is 496 energy levels. Collapsing D along the spectral dimension provides a monochrome image (e.g., FIG. 1C), in which each pixel contains spectral intensity information obtained at each energy level. Collapsing D along the image dimension provides an energy spectrum (e.g., FIG. 1D), in which spatial information is lost but the spectrum accounts for spectral intensity information as a function of the energy level (measured in eV in FIG. 1D). Generally, a collapsed version of D is employed in conventional analysis. Here, the entire data matrix D is employed for global analysis.

The image can be of any useful dimension (e.g., a two-dimensional image having dimensions a by b, typically measured in pixels, such as 600 pixels by 800 pixels; or a three-dimensional voxel having dimensions a by b by c). In certain embodiments, the image can be a region of interest (ROI) of a larger image, and the ROI can also be of any useful dimension (e.g., a by b, typically measured in pixels, such as 25 pixels by 50 pixels). The dimensions a, b, and c can be any useful number (e.g., an integer that is one or more).

Image arrays can be transformed (or unfolded) into a data matrix D in any useful manner. For instance, take an image array including n images, where each image has a dimension of a by b pixels (in the x-y plane). Each image can be rastered in the x-y plane to identify an intensity data point associated with each pixel, and then these data points can be strung out as a single vector having a length of a times b. This vector can be provided as a column in a matrix, where the column has a length of m=a times b. Repeating this process for each $n^{th}$ image then provides n number of columns, each column of length m. Mathematically, these data can be represented as an m×n data matrix D having m rows and n columns, in which each element $d_{m,n}$ in the matrix represents a data point from a single pixel located at an (x,y) position at a particular $n^{th}$ energy level.

Unfolding techniques can also be applied to arrays of higher dimensional information, such as a three-dimensional voxel including three spatial coordinates (i.e., the x-, y-, and z-coordinates) or a three-dimensional datum including two spatial and one temporal coordinates. For instance, take an image array including n images, where each image has a dimension of a by b by c pixels (in the x-y-z space). Then, the data matrix D can be represented as an m×n matrix, in which m=a times b times c, in which each image is rastered in the x-y plane for each $c^{th}$ step along the z-axis to produce a vector having a length of m. After repeating for each $n^{th}$ energy level, these data can be represented as an m×n data matrix D having m rows and n columns, in which each element $d_{m,n}$ in the matrix represents a data point from a single pixel located at an (x,y,z) position at a particular $n^{th}$ energy level. Additional details on unfolding higher dimensional data are described in Kotula P G et al., "Tomographic spectral imaging with multivariate statistical analysis: comprehensive 3D microanalysis," *Microsc. Microanal.* 2006; 12:36-48, which is incorporated herein by reference in its entirety.

In general, a chemical test sample can be analyzed with any useful spectroscopic method (e.g., any described herein) in order to obtain a set of images or spectra that captures emission signals of that sample when excited by a particular energy level. In brief, for NEXAFS, the chemical sample is irradiated with an X-ray source, thereby allowing for photoabsorption of the X-ray by the sample. This photoabsorption process results in a photoelectron that is excited to its next permitted energy level, as well as a core hole that is filled by radiatively emitting a fluorescence photon or by non-radiatively emitting an Auger electron. Emission signals can detected in any useful manner, such as by employing a channeltron, an energy analyzer, a scanning electron microscope, a photodetector (e.g., a charge-coupled device), or a fluorescence detector in order to produce one or more spectra or images. Such spectra or images, in turn, can be analyzed by any method herein to determine the type of electron transitions (e.g., is 1s→π* or σ* transitions) associated with an emission signal. Different chemical bonds exhibit different emission signals, which can be characterized by the energy level providing that signal or a line shape of the signal, as well as the $E_0$ associated with that signal. In this way, the chemical characteristics of the sample can be determined.

The present invention can be employed for any useful chemical test sample, such as a polymer, a thin film, a liquid, a gas, an adsorbate, an absorbate, a molecular complex, etc. In particular embodiments, the test sample can include low atomic number molecules (e.g., an atomic number less than 10 or 18, such as hydrogen, carbon, nitrogen, oxygen, and/or fluorine).

The image and the resultant image array can include any useful spectrum of a chemical test sample. Exemplary spectra include one or more one or more X-ray absorption spectra, near edge X-ray absorption fine structure spectra (NEXAFS), X-ray photoelectron spectra, energy dispersive X-ray spectra (EDS), Auger electron spectra, X-ray fluorescence spectra, proton-induced X-ray emission spectra, fluorescence spectra, infrared spectra, raman spectra, ultraviolet photoelectron spectra, photon emission spectra, mass spectroscopy spectra (e.g., time of flight-secondary ion mass spectroscopy (TOF-SIMS) or matrix-assisted laser desorption ionization secondary ion mass spectroscopy (MALDI-SIMS)), and/or photon absorption spectra. Additional chemical test samples, as well as spectra, are described in Hähner G, "Near edge X-ray absorption fine structure spectroscopy as a tool to probe electronic and structural properties of thin organic films and liquids," *Chem. Soc. Rev.* 2006; 35:1244-55; Outka D A et al., "Curve fitting analysis of near-edge core excitation spectra of free, adsorbed, and polymeric molecules," *J. Chem. Phys.* 1988; 88:3539-54; and Penner-Hahn J E, "X-ray absorption spectroscopy," in *Comprehensive Coordination Chemistry, Vol. II* (eds.-in-chief J. A. McCleverty and T. J. Meyer; vol. ed. A.B.P. Lever), Elsevier Ltd., Amsterdam, Netherlands, 2003, pp. 159-86, chp. 2.13, each of which is incorporated herein by reference in its entirety.

Analytical Model for Chemical Data

Figure 2A:
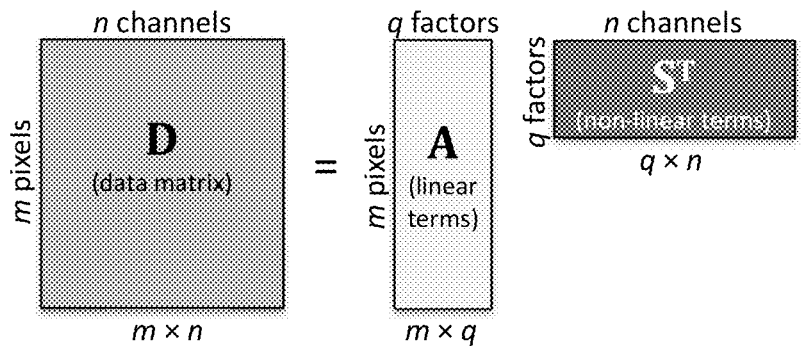
FIG. 2A-2C shows an exemplary analytical model and its factors. Provided are an analytical model for the data matrix D by a combination of matrix A including linear terms and matrix S including non-linear terms, where superscript $T$ denotes transpose (FIG. 2A); as well as two exemplary factors for describing a spectrum, such as a Gaussian peak factor $I_G$ (FIG. 2B) and a shaped step factor $I_S$ (FIG. 2C) with its associated linear and non-linear terms.

We developed an analytical model to mathematically represent the complex phenomenon captured by chemical data. This analytical model accepts the use of non-linear and linear terms to describe spectral peaks or emissions observed in the data matrix. The line shape of many spectral emissions can be described by a mathematical expression, such as a Gaussian function, a step function, an offset function, etc. Two or more of these expressions, in turn, can be combined to describe an observed spectrum. Here, we propose an analytical model of data matrix D (FIG. 2A), which can be expressed mathematically as follows:

$$D = AS^T, \quad (\text{Eq. 1})$$

where D is an m×n data matrix, A is an m×q matrix including linear terms, and S is a n×q matrix including non-linear terms. As described herein, m is the number of pixels for an image (or region of an image) under analysis, and n is the number of energy levels. The term q represents the number of factors that adequately characterize (e.g., as determined by one or more convergence metrics or criteria described herein) the data matrix D. Also, as used herein, superscript T represent matrix transpose.

Any useful factor can be employed to characterize the spectral emission. For instance, many spectra can be characterized by a Gaussian function ($I_G$), a Lorentzian function ($I_L$), a pseudo-Voigt function ($I_V$), an asymmetric peak function (any factor (e.g., $I_G$, $I_L$, $I_V$, or $I_S$) modified to have w=mE+b, where energy level E is the variable and m and b are constants that are common to all shifted peaks), a shaped step function ($I_S$), and/or an offset function ($I_O$). Each of these functions can be employed as a factor in the methods herein. In most situations, two or more of these factors (i.e., q is more than or equal to 2) are employed together to describe spectral information in the data matrix. Exemplary factors are as follows:

Gaussian:

$$I_G = Ae^{-\left(\frac{E-E_0}{w}c\right)^2}; \quad (\text{Eq. 2a})$$

Lorentzian:

$$I_L = A\left(\frac{(w/2)^2}{(E-E_0)^2 + (w/2)^2}\right); \quad (\text{Eq. 2b})$$

Pseudo-Voigt:

$$I_V = A\left[\eta\left(\frac{(w/2)^2}{(E-E_0)^2 + (w/2)^2}\right) + (1-\eta)e^{-\left(\frac{E-E_0}{w}c\right)^2}\right]; \quad (\text{Eq. 2c})$$

Asymmetric peak: Set w=mE+b; (Eq. 2d)

Asymm. Gaussian:

$$I_{A-G} = Ae^{-\left(\frac{E-E_0}{mE+b}c\right)^2}; \quad (\text{Eq. 2d-1})$$

Asymm. Lorentzian:

$$I_{A-L} = A\left(\frac{(mE+b/2)^2}{(E-E_0)^2 + (mE+b/2)^2}\right); \quad (\text{Eq. 2d-2})$$

Shaped step:

$$I_S = A\left[\frac{1}{2} + \frac{1}{2}\text{erf}\left(\frac{E-E_0}{w}d\right)\right]; \text{ and} \quad (\text{Eq. 2e})$$

Offset:

$$I_O = A; \quad (\text{Eq. 2f})$$

where for each of these factors, energy level E is the variable and term A (a linear term) is an amplitude of a peak for each factor. Additional terms include an energy value $E_0$ at a position in the center of a peak or step for each factor, a constant c (e.g., where c=2√log 4 or 2√ln 4 when w is a full width at half maximum or FWHM), a full width w at half maximum of a peak for each factor, a constant η (where 0<η<1), a constant m that scales w, a constant b that shifts w, and a decay coefficient d (e.g., an exponential decay coefficient, such as d=2√log 2). For the asymmetric peak function, term w can be replaced with mE+b for any symmetric peak function (e.g., the Gaussian, Lorentzian, pseudo-Voigt, or shaped step factors). As can be seen, most factors (except the offset factor in Eq. 2f) include a linear term (e.g., term A in the Gaussian factor $I_G$ of Eq. 2a) and a non-linear term (e.g., term exp[-((E-E_0)c/w)^2] for the Gaussian factor $I_G$ of Eq. 2a).

Figure 1D:
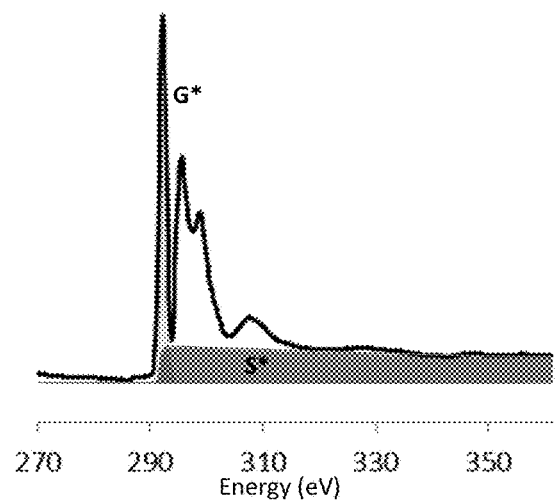
Figure 2B:
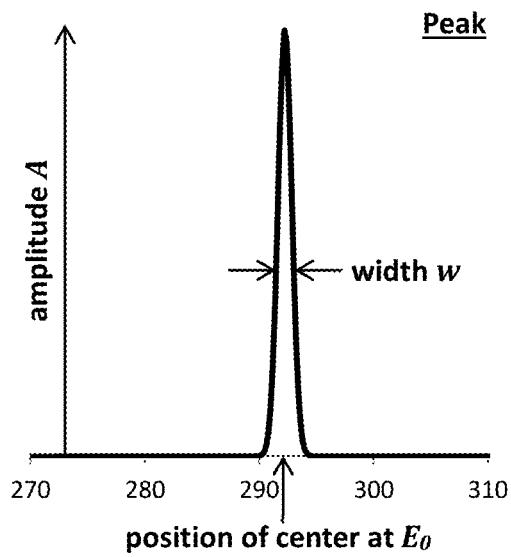
Figure 2C:
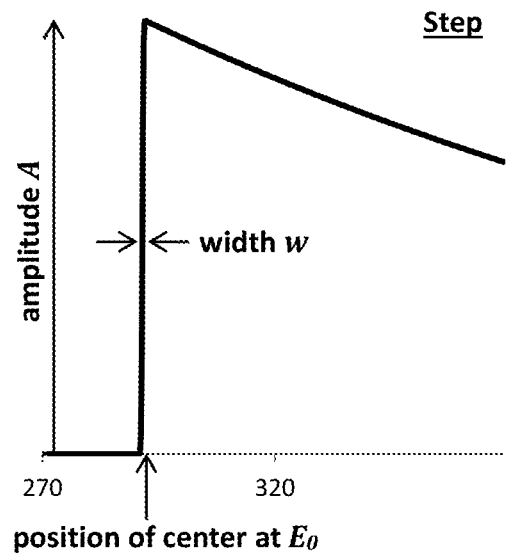
Figure 16:
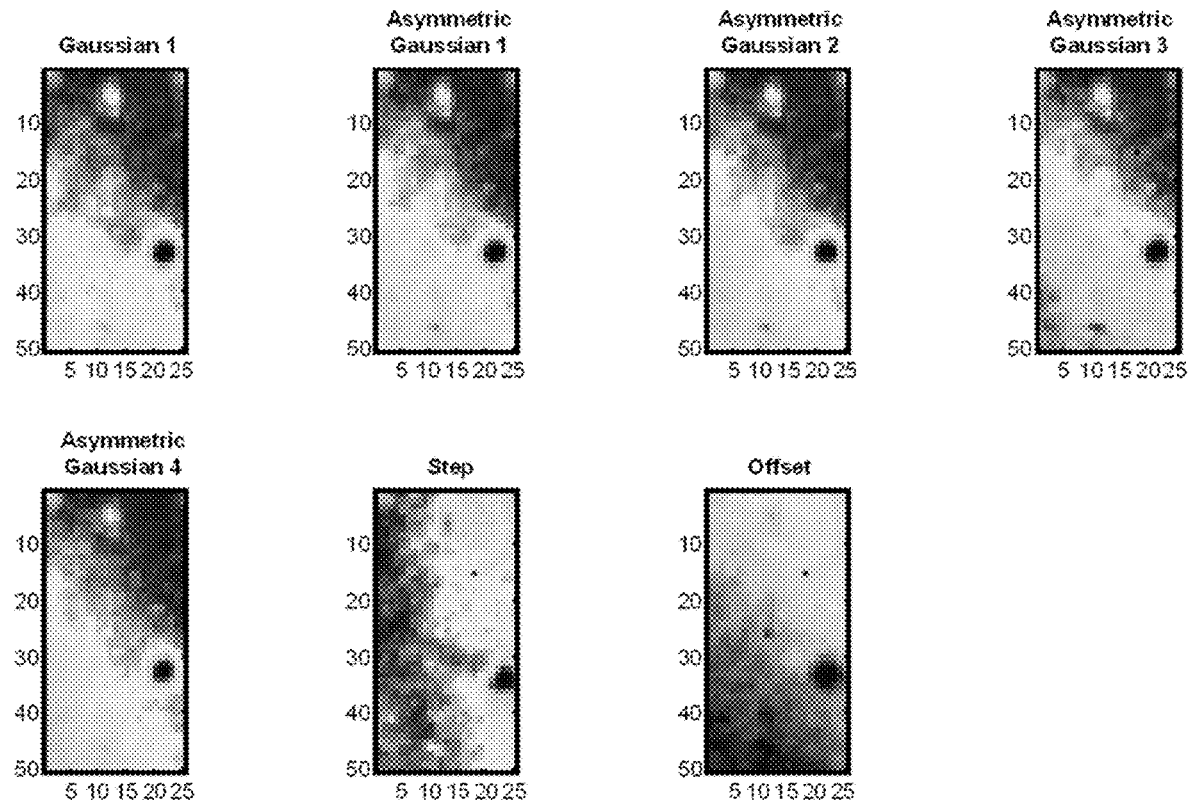
FIG. 16 shows reconstructed images of 7 factors used to characterize the PTFE sample. These 7 factors include factor 1 (a Gaussian fit), factor 2 (a first asymmetric Gaussian fit), factor 3 (a second asymmetric Gaussian fit), factor 4 (a third asymmetric Gaussian fit), factor 5 (a fourth asymmetric Gaussian fit), factor 6 (a step fit), and factor 7 (an offset).

Each spectral feature (e.g., peak, emission, step, etc.) can be modeled by a factor. For instance, FIG. 1D shows an exemplary spectrum having various peaks and steps, in which one peak has a maximum intensity at about 292 eV (labeled G* and shaded with light gray) and another region has a step that spans from about 290 eV to about 360 eV (labeled S* and shaded with dark gray). These two features (G* and S*) can be most accurately described by a Gaussian factor and a shaped step factor, respectively. These features and factors can be described mathematically, as shown in FIG. 2B-2C. The Gaussian factor $I_G$ in FIG. 2B is characterized by three terms: an amplitude A of the peak, a full width w at half maximum of the peak, and an energy value $E_0$ at a position in the center of the peak; and the expression for the Gaussian factor is provided in FIG. 2B as well as Eq. 2a. The shaped step factor $I_S$ in FIG. 2C is characterized by four terms: an amplitude A of the peak, a full width w at half maximum of the step, an energy value $E_0$ at a position in the center of the step, and an decay coefficient d; and the expression for the shaped step factor is provided in FIG. 2C as well as Eq. 2e. By combining these two factors, two spectral features of the spectrum in FIG. 1D can be described. Additional factors can then be modeled within matrices A and S, as needed, to fit all of the features in the spectrum, as described in FIGS. 16 and 17 and its associated text.

Using the analytical model of Eq. 1, we can identify estimates or solutions for matrices A and S that accurately describe the real data matrix D in a global analysis manner. First, we select a set of factors (e.g., Eqs. 2a-2f) that can be used to represent a spectral feature provided in the data matrix D. Then, we construct matrix A to include all linear terms for each of the q factors selected to represent the data, as well as construct matrix S to include all non-linear terms for each of the q factors. Next, as S includes non-linear terms, a non-linear solver is employed to identify an estimate or solution for S. In S, each non-linear term for each factor is computed using estimated values for each term (e.g., $E_0$, w, and c terms for Gaussian factor $I_G$ in Eq. 2a) and the given energy axis n (e.g., as the variable E in Eq. 2a). The offset, which lacks non-linear terms, is entered as a column of ones. Provided the estimated matrix for S, a linear solver (e.g., using least squares) is employed to identify an estimate or solution for A. Optionally, constraints (e.g., non-negativity or equality constraints) can be imposed for each solution of S and/or A. Estimates for A, S, and q can be refined by using any useful method, such as by applying the least squares criterion (e.g., as described herein) and by iterating such refinement steps until convergence. Additional details for applying global analysis are described herein.

This analytical model provides numerous benefits. For instance, many conventional non-linear least squares methods can be applied in a global analysis manner but with an immense computational burden. In contrast, the analytical model herein separates the solving step for the non-linear terms in S from the solving step for linear terms in A. This distinctive feature of the analytical model results in an efficient method to analyze complex, multidimensional data. Take an example of a data matrix $D_G$ that is characterized four Gaussian-type peaks, where each peak is represented by one Gaussian factor and each Gaussian factor has one linear term (i.e. A in Eq. 2a) and two non-linear terms (i.e., $E_0$ and w in Eq. 2a). In addition, the data matrix $D_G$ includes an image array having n number of images, in which each image has 100 pixels (i.e., m=100). Using conventional non-linear solving methods, the non-linear solver would have to solve for 1,200 different terms for each iteration, which is determined as follows:

$$\frac{4 \text{ Gaussian peaks}}{m^{th} \text{ pixel}} \times \frac{3 \text{ factor terms}}{\text{Gaussian peak}} \times 100 \text{ pixels} = 1{,}200 \text{ terms.} \quad \text{(Eq. 3)}$$

If additional iterations are needed (i.e., i more than 1), then the conventional method would require a solution of 1,200 terms for each iteration or 1,200×i number of terms. In contrast, using the analytical method herein, the number of terms requiring a solution is drastically decreased. Taking the same data matrix $D_G$ above, the analytical method herein requires a solution of only 408 terms:

Non-linear solutions:

$$\frac{4 \text{ Gaussian peaks}}{m^{th} \text{ pixel}} \times \frac{2 \text{ non-linear factor terms}}{\text{Gaussian peak}} = 8 \text{ terms in } S; \quad \text{(Eq. 4a)}$$

Linear solutions:

$$\frac{4 \text{ Gaussian peaks}}{m^{th} \text{ pixel}} \times \frac{1 \text{ linear factor term}}{\text{Gaussian peak}} \times 100 \text{ pixels} = 400 \text{ terms in } A; \quad \text{(Eq. 4b)}$$

and

Total solution: 8 terms in S+400 terms in A=408 total terms. (Eq. 4c)

Thus, the number of terms in a conventional analysis scales linearly as the number of spectral features (or factors representing such features), the number of terms for each factor representing such features, and the size of the data matrix. In contrast, the present methods do not exhibit such linear scaling because the solution for non-linear terms does not depend on the number of image pixels. This reduction in the number of terms can have drastic implications on computation efficiency for bigger data matrices, as well as methods requiring numerous iterations.

Global Analysis

Figure 3:
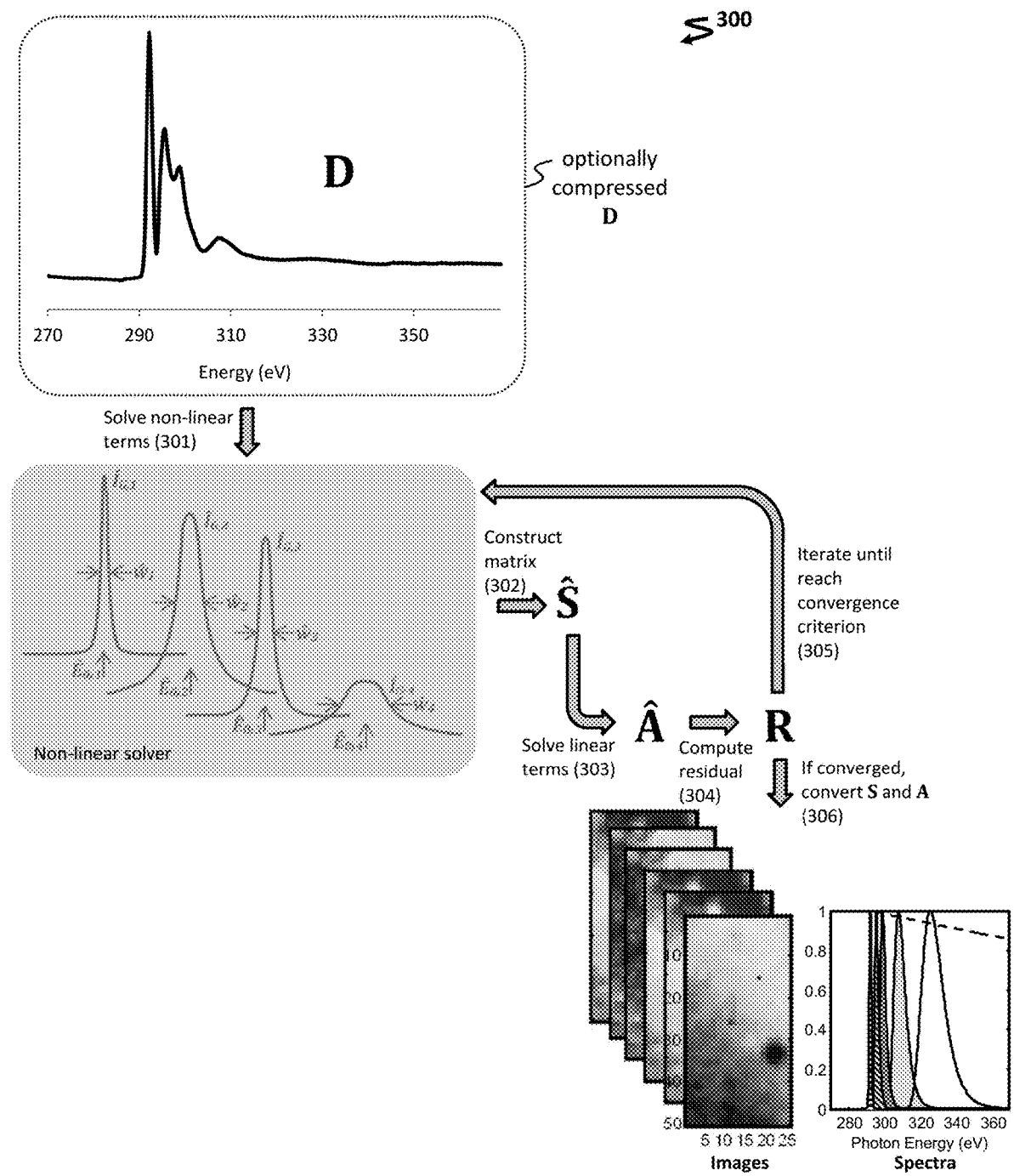
FIG. 3 shows an exemplary method 300 for analyzing a chemical test sample characterized by the data matrix D.

Upon obtaining data matrix D (e.g., as described herein), global analysis can be performed to obtain matrices A and S that describe the chemical signatures of the underlying chemical test sample. FIG. 3 provides an exemplary method 300 for implementing global analysis of a data matrix D, which can be optionally compressed (e.g., using PCA, as described herein). The method includes a first step 301 of solving for non-linear terms of factor(s) using the data matrix D; a second step 302 of constructing the estimated matrix Ŝ for matrix S using those non-linear terms; a third step 303 of solving for linear terms of factor(s) to an provide estimated matrix Â; a fourth step 304 of computing a residual matrix R characterizing the difference or error between the real data matrix D and the estimated matrices Ŝ and Â; an iteration step 305 of repeating any useful step until convergence; and a final step 306 of converting the converged matrices into a readily interpretable image or spectrum. Details for these steps follow.

The method employs a non-linear solver to solve 301 non-linear terms within the selected factors. As seen in FIG. 3, the exemplary factors are represented as estimated factors for a Gaussian function, which includes estimated factors $\hat{I}_{G,1}$, $\hat{I}_{G,2}$, $\hat{I}_{G,3}$, and $\hat{I}_{G,4}$ having estimated terms $\hat{E}_{0,1}$ and $\hat{w}_1$ for factor $\hat{I}_{G,1}$; $\hat{E}_{0,2}$ and $\hat{w}_2$ for factor $\hat{I}_{G,2}$; $\hat{E}_{0,3}$ and $\hat{w}_3$ for factor $\hat{I}_{G,3}$; and $\hat{E}_{0,4}$ and $\hat{w}_4$ for factor $\hat{I}_{G,4}$. Each peak in the data matrix D can be computed using the estimated terms and the given energy axis represented by n. Based on these estimated factors and non-linear terms, an estimated matrix Ŝ for matrix S is constructed 302, in which Ŝ is dimensioned as n number of spectral channels (or energy levels) by q number of factors.

Any useful methodology can be employed to solve for S. Many non-linear solving methods are iterative procedures, in which initial estimates (e.g., a provided estimate or a random estimate) are further refined by minimization (e.g., by least squares, by damped least squares, etc.). Exemplary methods include the Levenberg-Marquardt method, the Gauss-Newton method, the gradient descent method, the steepest descent method, other non-linear least squares minimization methods, as well as computer-implementations of such methods, including lsqnonlin, a MATLAB® function that uses the Levenberg-Marquardt algorithm, as well as those described in Beechem J M, "Global analysis of biochemical and biophysical data," *Methods Enzymol.* 1992;

210:37-54, which is incorporated herein by reference in its entirety. Solutions for S or refinement of S can be obtained by using least squares, as follows:

$$\min_S \|D^T - AS^T\|_F^2, \quad \text{(Eq. 5)}$$

where subscript F represents the Frobenius norm, D is the data matrix, superscript $^T$ is matrix transpose, A is any useful matrix of linear terms, and S is any useful matrix of non-linear terms.

Given $\hat{S}$ (e.g., $S_i$, $\hat{S}_{initial}$, or $\hat{S}$) the linear terms of D are solved 303 and employed to construct estimated matrix $\hat{A}$, which is dimensioned as m number of image pixels by q number of factors. In one instance, estimated matrix $\hat{A}$ can be determined as follows:

$$\hat{A} = DS(\hat{S}^T\hat{S})^{-1}, \quad \text{(Eq. 6)}$$

where $\hat{S}$ is an estimated matrix for S. In other instances, A can be obtained using least squares, which can be formally described as follows:

$$\min_A \|D - AS^T\|_F^2. \quad \text{(Eq. 7)}$$

In another instance, matrix A can be described as follows:

$$A = X\tilde{A}, \quad \text{(Eq. 8)}$$

where X is a matrix having mutually orthogonal columns (e.g., such as score matrix T, as further described herein) and $\tilde{A}$ is an estimator matrix for matrix A.

Any useful methodology can be used to solve for matrix A. In one instance, eigenanalysis of the data matrix D, the covariance matrix $D^TD$, or the association matrix $DD^T$ is employed. In another instance, principal component analysis is employed, e.g., as described herein. In yet another instance, orthogonal projection methods are employed, in which vector projection is used to generate approximations for A. Although the exemplary method 300 describes an estimate of S to precede the estimate for A, these steps can be reversed. For instance, the first step can include an estimate for A, which can be used in turn to provide an estimate of S.

To determine the accuracy of the estimated matrices, a residual matrix R can be computed 304. Matrix R can be computed in any useful manner. In one instance, R is determined as follows:

$$R = D - \hat{A}\hat{S}^T, \quad \text{(Eq. 9a)}$$

where estimated matrices $\hat{A}$ and $\hat{S}$ are compared against the real data matrix D. In another instance, R is determined as follows:

$$R = \hat{A} - D\hat{S}(\hat{S}^T\hat{S})^{-1}, \quad \text{(Eq. 9b)}$$

which can be mathematically rearranged to be equivalent to Eq. 9a. However, Eq. 9b requires manipulation of m×q matrices (for instance, R is an m×q matrix), and Eq. 9a require matrix addition of the entire data set D that is an m×n matrix. In most instances, q will be less than n. The residual matrix R, in turn, can be used to determine convergence as compared to an appropriate convergence criterion (e.g., a sum squared residual SSR), as described herein.

To ensure that the estimated matrices S and A appropriately model the real data, steps 301, 302, 303, and 304 (performed in any useful order) can be iterated 305 as needed until convergence. Iterations can include estimating matrix $\hat{A}$ and then matrix $\hat{S}$, or vice versa. As used herein, a carat (ˆ) indicates an estimated matrix, and a subscript i indicates a matrix produced at an $i^{th}$ iteration. In some instances, i is the number of iterations until convergence. For instance, a first matrix of S is indicated as $S_1$; an $i^{th}$ matrix of S is indicated as $S_i$, where i is the number of iterations (e.g., until convergence); an estimated matrix of S is indicated as $\hat{S}$; and an initial matrix of S, which is a matrix having estimated non-linear terms, is indicated as $\hat{S}_{initial}$.

Upon obtaining an estimate for A (e.g., $A_i$, $\tilde{A}$, $\hat{A}_{initial}$, or $\hat{A}$) or S (e.g., $S_i$, $\hat{S}_{initial}$, or $\hat{S}$), further processes can be employed to refine this estimate, such as by using iterative constrained least squares methods, as described herein. Assuming an initial estimate or solution for S and/or A, the methods herein can be iterated until convergence. In one instance, a first matrix $S_1$ can be used to solve for A (e.g., using Eqs. 1, 6, and/or 7), thereby providing a first matrix $A_1$. Using this computed matrix $A_1$, the first matrix $S_1$ can be refined to provide a second matrix $S_2$. In this iterative fashion, matrices S and A can be solved (e.g., by least squares, such as according to Eqs. 5 or 7) until the convergence criterion has been met. Thus, the methods herein can include i number of iterations to provide an estimated matrix $S_i$ and $A_i$ at each $i^{th}$ iteration step until convergence.

Although examples are provided with an initial matrix S to solve for A, the converse can be true. For instance, a first matrix $A_1$ can be used to solve for S, thereby providing a first matrix $S_1$. Then, using this computed matrix $S_1$, the first matrix $A_1$ can be refined to provide a second matrix $A_2$. These steps can be conducted in an iterative fashion until convergence. Additional details for these analytic methodologies are described in Keenan M R et al., "Algorithms for constrained linear unmixing with application to the hyperspectral analysis of fluorophore mixtures," *Proc. SPIE* 2002; 4186:193-202; Keenan M R, "Multivariate analysis of spectral images composed of count data," in *Techniques and Applications of Hyperspectral Image Analysis* (eds. H. F. Grahn and P. Geladi), John Wiley & Sons, Hoboken, N.J., 2007, pp. 89-126, chp. 5; and Andrew J J et al., "Rapid analysis of Raman image data using two-way multivariate curve resolution," *Appl. Spectrosc.* 1998; 52(6):797-807, each of which is incorporated herein by reference in its entirety.

Finally, upon reaching convergence, the obtained matrices S and A can be converted into an image array, a spectral array, or a spectrum that can be interpreted by a user. Conversion can be implemented in any useful manner, as described herein.

Additional steps can be performed during global analysis. Optionally, non-negativity constraints on each element of $S^T$ or A can be applied as follows:

$$S^T \geq 0 \text{ and/or} \quad \text{(Eq. 10a)}$$

$$A \geq 0. \quad \text{(Eq. 10b)}$$

Vector rotation may optionally be employed. For instance, Varimax rotation is one such vector rotation technique, in which factors are rotated to maximize the total variance of the squared vectors, while maintaining orthogonality between all vectors. Additional methods for orthogonal and non-orthogonal factor rotation include Quartimax, Quartimin, Equamax, Orthomax, Parsimax, Oblimax, Oblimin, and Promax, as well as any described in Harman H H, "Modern factor analysis," ($3^{rd}$ ed. rev.), The University of Chicago Press, Chicago, Ill., 1976, pp. 278-99; and Keenan M R, "Exploiting spatial-domain simplicity in spectral image analysis," *Surf Interface Anal.* 2009; 41:79-87, each of which is incorporated herein by reference in its entirety.

The data matrix can be processed in any useful manner prior to global analysis, such as by compressing, weighting, scaling, centering, etc., where one or more of these processes can be applied. In some instances, the data matrix can be centered by subtracting the mean of all the spectra from each individual spectrum prior to global analysis, data compression, and/or matrix factorization. In other instances, the data matrix can be weighted in order to reduce noise (e.g., noise exhibiting Poisson characteristics), such as by defining an alternate space in which uncertainty of the data in that alternate space is more uniform. An exemplary weighted method is described in Keenan M R et al., "Accounting for Poisson noise in multivariate analysis of ToF-SIMS spectrum images," *Surf Interface Anal.* 2004; 36:203-12, which is incorporated herein by reference in its entirety. In yet other instances, the data matrix can be adjusted for spectral background, such as by using the methods in U.S. Pat. Nos. 6,584,413 and 6,675,106, which is incorporated herein by reference in its entirety.

Computer-Implemented Methods for Global Analysis

The methods herein can be implemented in any useful manner. For instance, a spectrometer can be used to obtain spectral data, such as an array of images. In one example, the spectrometer is directly linked to a spectrum analyzer (e.g., via electrical or optical cable), or by wireless means, for "real-time" spectral analysis. Alternatively, the measured spectral data can be stored on computer readable memory means (e.g., CD-ROM, DVD, magnetic tape, etc.) and provided to a spectrum analyzer at a later time for off-line post-processing.

A spectrum analyzer can include any useful components, such as a computer processor; an operator interface (such as a keyboard or computer mouse); a memory for storing data and executable instructions; an interface for data input and output; an executable software instruction embodied in an executable computer program code; and a display for displaying the results of a global spectral analysis. The computer processor can be a standard laboratory Personal Computer (PC), for example, using an Intel fourth generation microprocessor, such as made by IBM, Compaq, Dell, etc.; or a workstation, such as made by SUN, HP, Silicon Graphics, etc., running UNIX or Linux operating systems. Software instructions can be expressed in any of a variety of well-known computer languages, including MATLAB®, FORTRAN, C, C++, and Java for implementing any useful program, subroutines, subprograms, and input/output routines.

In another instance, the methods and steps herein are implemented using a computer. In particular, receiving steps can be implemented by a processor configured to receive input (e.g., data input) from a spectrometer (e.g., a detector of the spectrometer). Other steps (e.g., generating of one or more matrices, spectra, or images; performing global analysis; compressing data; computing matrices, eigenvalues, or eigenvectors; iterating; and/or converting matrices into one or more other matrices, spectra, or images) can be implemented by a processor optionally having memory to store data and/or executable instructions, software instructions embodying executable instructions (e.g., for generating, performing, converting, iterating, solving, computing, compressing, etc., according to the methods described herein), and an output (e.g., a display) to show any useful result to the user.

Figure 4A:
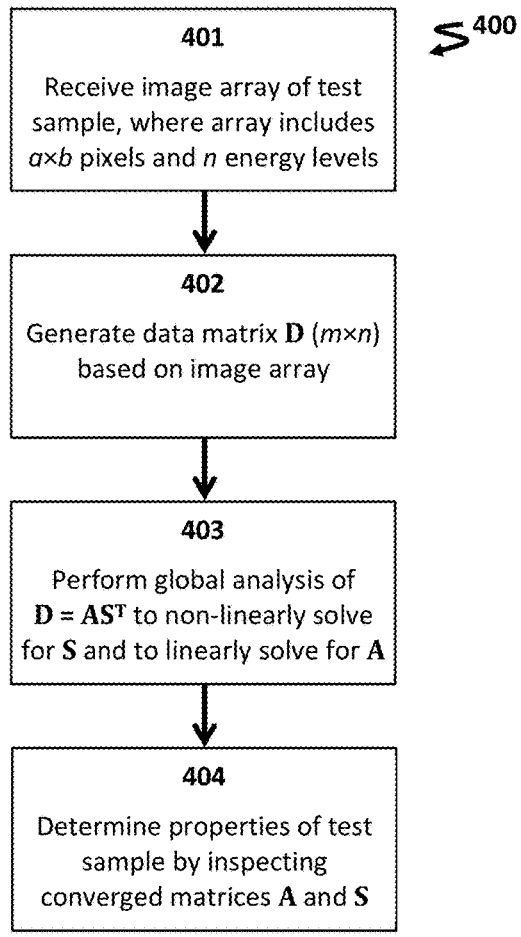
FIG. 4A-4B shows an exemplary method 400 for global analysis of data for a chemical test sample (FIG. 4A); and a graphic representation of applying the least squares criterion to the data matrix D in order to obtain estimated matrices for S and A (FIG. 4B).
Figure 4B:
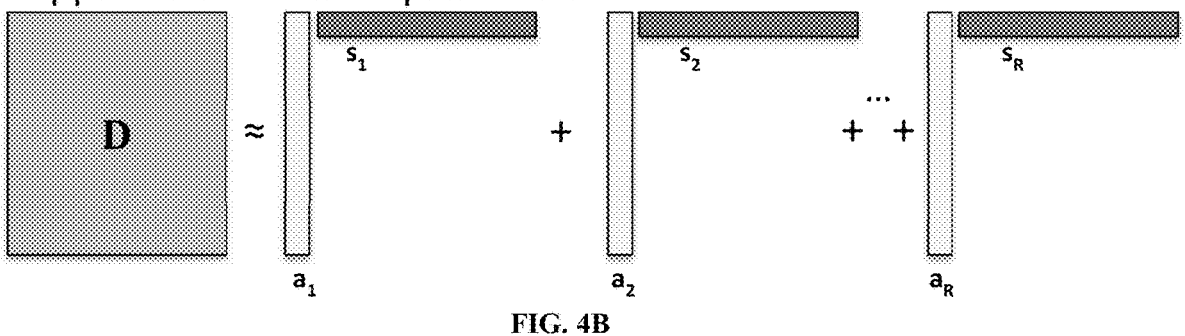

FIG. 4A-4B shows an exemplary method for performing global analysis, and FIG. 5A-5D shows exemplary computer-implementations of that method. As seen in FIG. 4A, the global analysis method 400 includes numerous steps, including a step 401 of receiving an image array of a test sample, where array includes a plurality of images. Each image has a×b pixels, and one image is captured for each n energy levels, thereby providing n number of images. The next step 402 includes generating a data matrix D (m×n) based on the image array by unfolding, as described herein, where m is a times b. The third step 403 includes performing global analysis, as described herein, of $D=AS^T$ (Eq. 1) in order to (i) non-linearly solve for S and (ii) linearly solve for A, where (i) and (ii) can be performed in any order or at the same time. The fourth step 404 includes determining one or more properties of test sample (e.g., chemical properties, bonding properties, etc.) by inspecting converged matrices A and S (e.g., including converted versions of matrices A and S). Optionally, the global analysis step 403 includes applying a least squares criterion to A and/or S, such that D can be represented as in FIG. 4B. Each of these steps can be performed using a computer, a processor, a memory, a program code, etc.

Figure 5A:
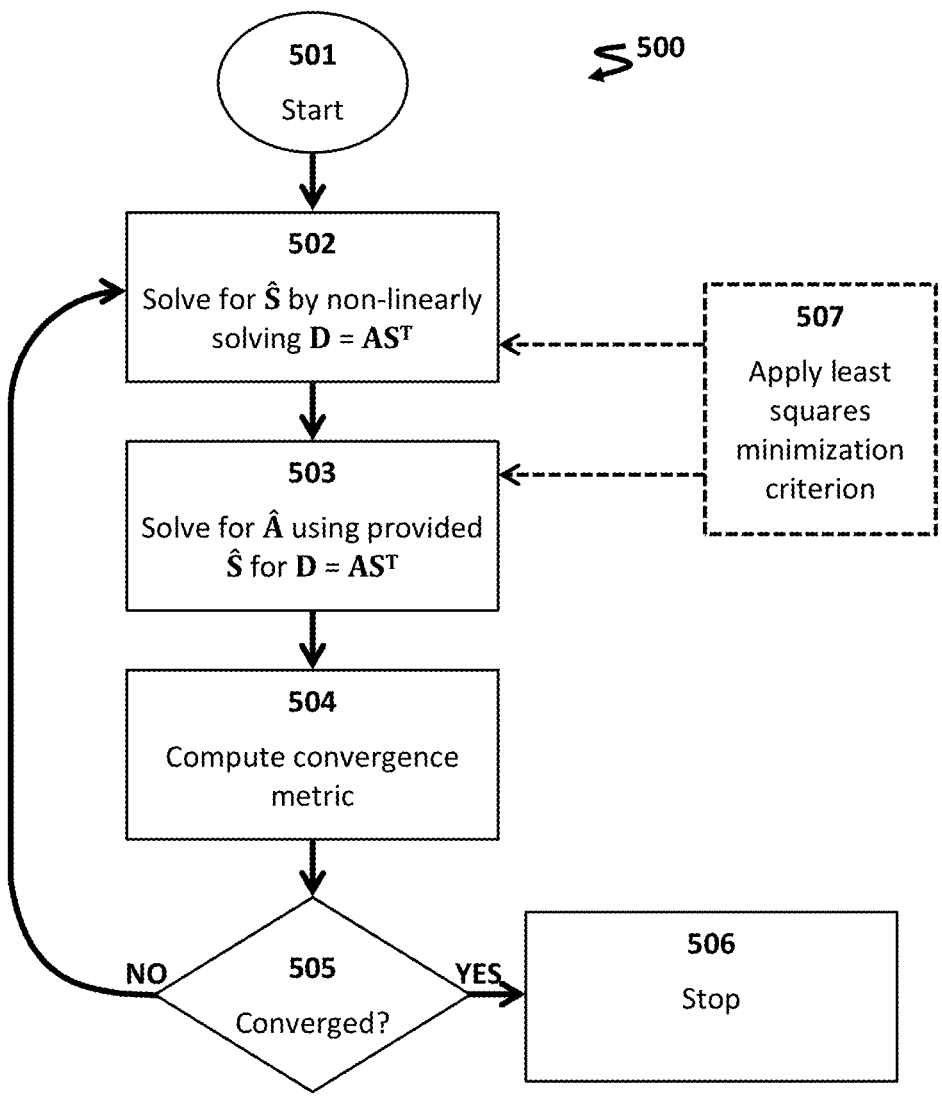
FIG. 5A-5D shows exemplary computer-implemented methods for global analysis. Provided are a first non-limiting method 500 to provide estimated matrices $\hat{S}$ and $\hat{A}$ (FIG. 5A); a second non-limiting method 5000 that employs a residual matrix R to determine convergence (FIG. 5B); a third non-limiting method 5100 that employs an initial matrix $\hat{S}_{initial}$ to arrive at an estimated matrix $\hat{S}$ (FIG. 5C); and a fourth non-limiting method 5200 that employs an initial matrix $\hat{S}_{initial}$ to solve for an estimated matrix $\hat{A}$ (FIG. 5D).

Methods herein can be implemented on a computer, such as by a processor of the computer that is configured to perform executable instructions, by a memory to store data and such executable instructions, and by an executable computer program code embodying such instructions. One exemplary computer-implemented method 500 includes a routine of steps capable of being programmed in any useful computer code language (FIG. 5A). The method 500 includes a start prompt 501 to launch the global analysis method; a step 502 of solving for an estimated matrix $\hat{S}$ by non-linearly solving $D=AS^T$; a step 503 of solving for an estimated matrix $\hat{A}$ using the estimated matrix $\hat{S}$ as S in the following equation $D=AS^T$ or any other useful equation described herein (e.g., Eqs. 6, 7, and 8); a step 504 of computing a convergence metric; and a decision step 505 of determining whether the convergence metric meets the convergence criterion. If converged, then a stopping step 506 ends the routine. If not converged, then the routine is iterated until convergence. Optionally, a step 507 includes applying a least square minimization criterion to either solving steps 502,503 for matrices $\hat{S}$ and/or $\hat{A}$.

Figure 5B:
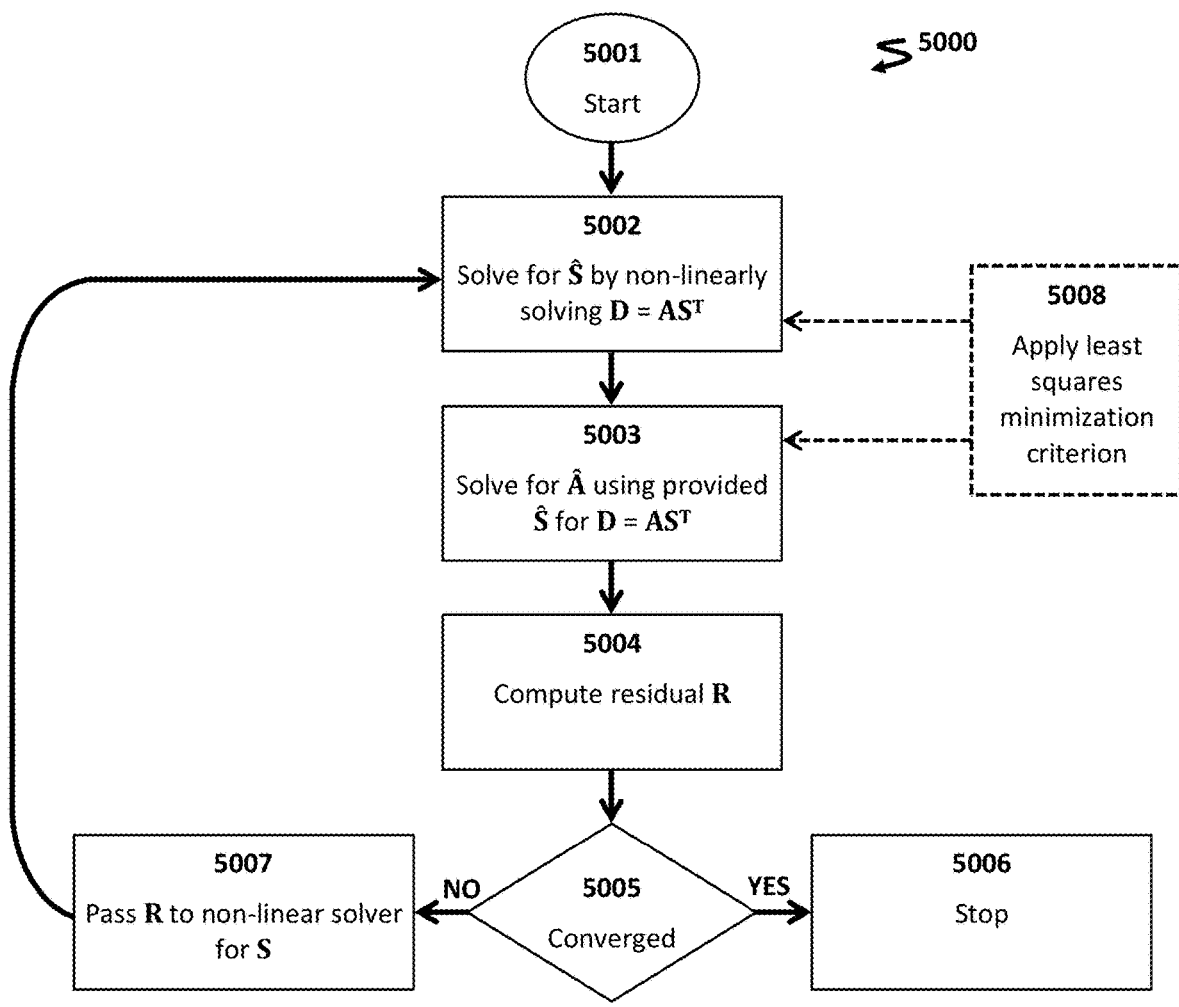

Other useful routines can be implemented to include any other useful step. For instance, the method can include the step of computing a residual matrix R as a convergence metric to characterize convergence. FIG. 5B shows an exemplary method 5000 including a start prompt 5001 to launch the global analysis method; a step 5002 of non-linearly solving for an estimated matrix $\hat{S}$; a step 5003 of linearly solving for an estimated matrix $\hat{A}$; a step 5004 of computing a residual matrix R (e.g., using any useful method herein, such as Eqs. 9a, 9b, 21, 23, 24a, 25a, and/or 25b); and a decision step 5005 of determining whether the convergence metric meets the convergence criterion. If converged, then a stopping step 5006 ends the routine. If not converged, then the computed residual matrix R is employed to solve for a further estimated matrix $\hat{S}$. To effect this step, the residual matrix R is passed 5007 to the non-linear solver for S, such that matrix R is further minimized to provide improved estimates for S. The routine is then iterated until convergence. Optionally, a step 5008 includes applying a least square minimization criterion to either solving steps 5002,5003 for matrices $\hat{S}$ and/or $\hat{A}$.

Figure 5C:
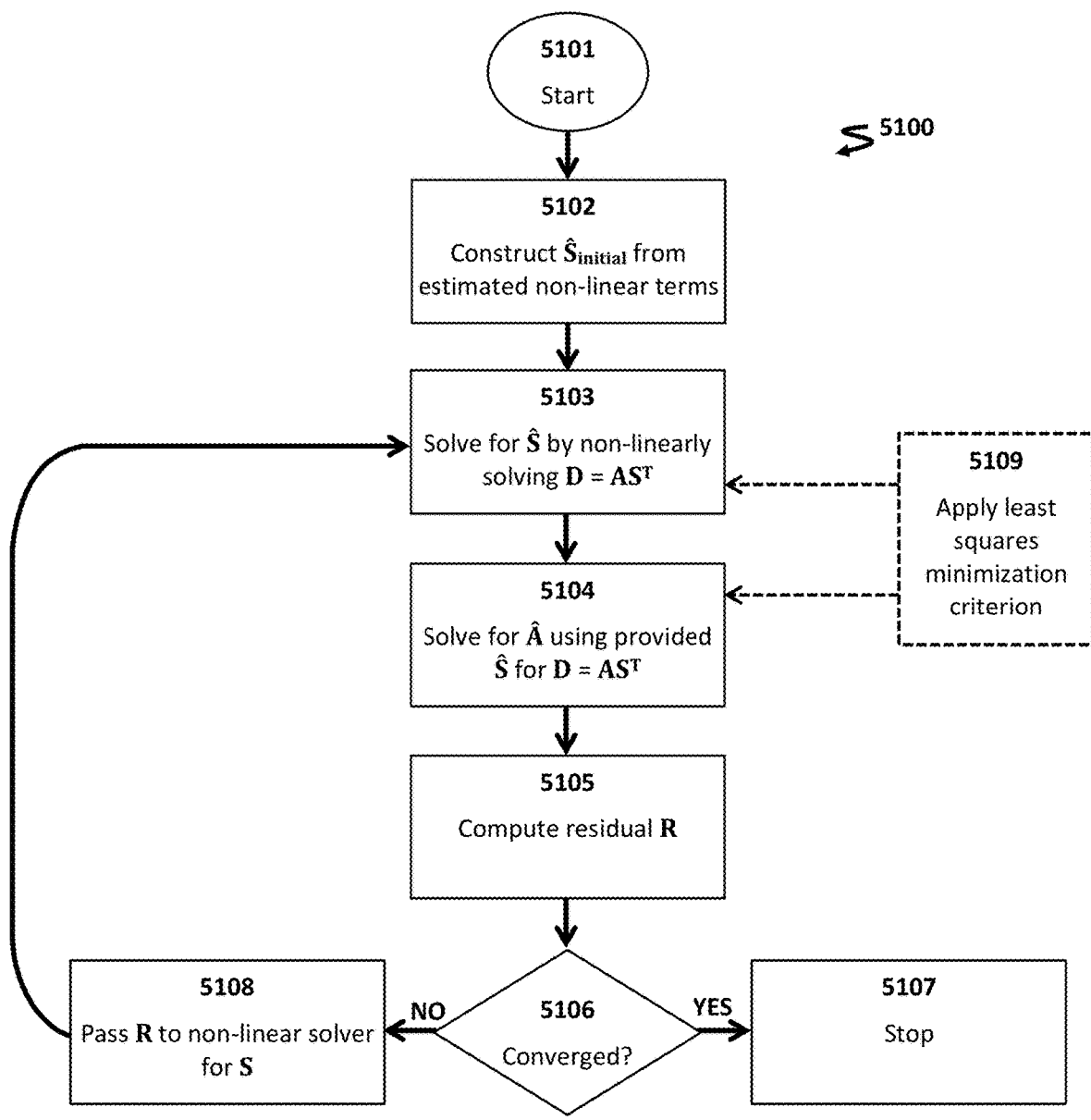
Figure 5D:
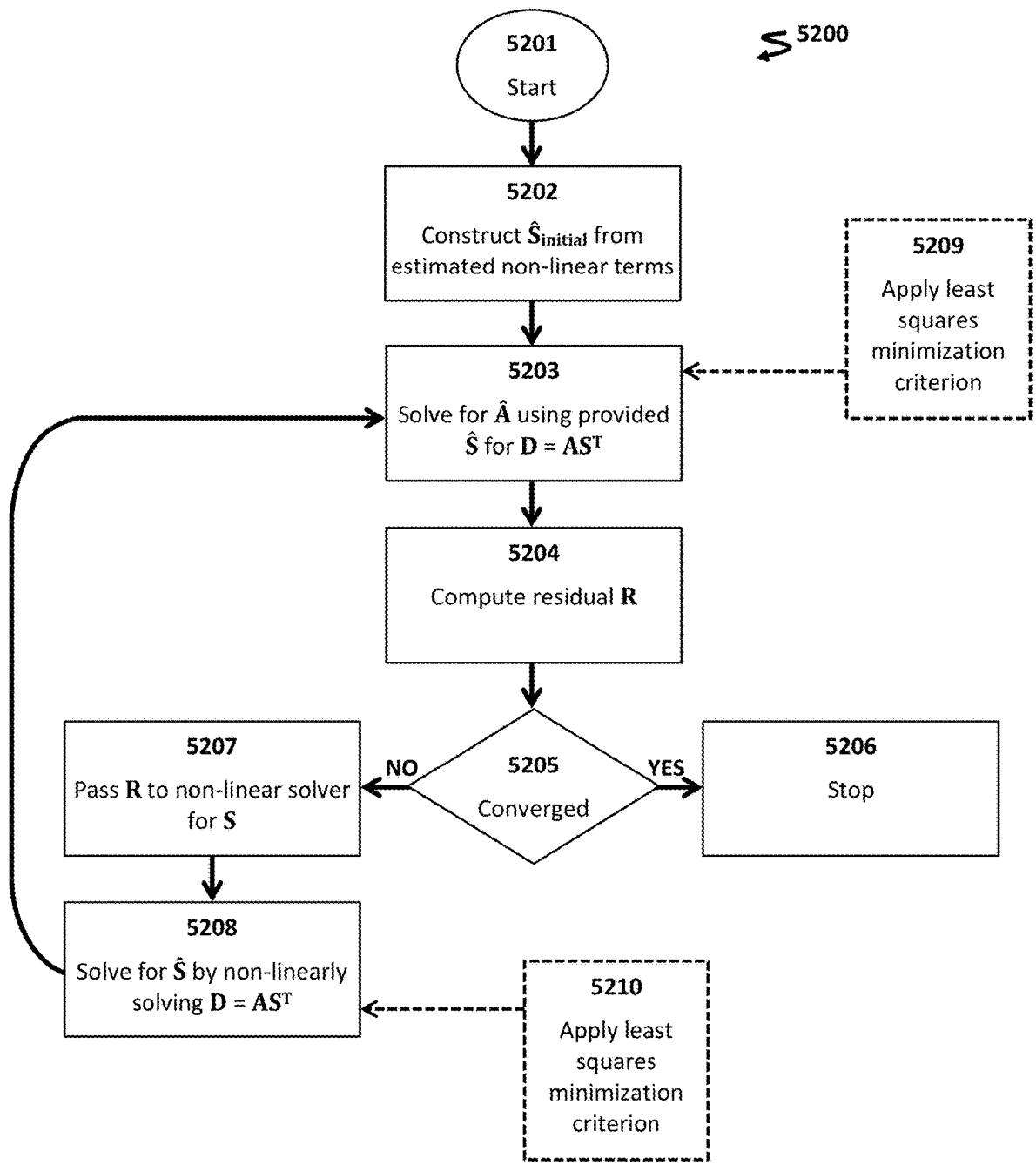

At times, an initial estimate for S can be provided, such as when the chemical sample is composed of a known polymer with known spectral peaks. To expedite computation, an initial estimate for such features can be provided as an initial matrix $\hat{S}_{initial}$ composed of expected non-linear terms. FIG. 5C-5D provides exemplary computer-implemented methods 5100,5200 including such an initial matrix.

Exemplary method 5100 (FIG. 5C) includes a start prompt 5101 to launch the global analysis method; a step 5102 of constructing initial matrix $\hat{S}_{initial}$ from estimated non-linear term; a step 5103 of non-linearly solving for an estimated matrix $\hat{S}$ by starting from the estimated non-linear terms provided as $\hat{S}_{initial}$; a step 5104 of linearly solving for an estimated matrix $\hat{A}$; a step 5105 of computing a residual matrix R (e.g., using any useful method herein, such as Eqs. 9a, 9b, 21, 23, 24a, 25a, and/or 25b); and a convergence decision step 5106. If converged, then a stopping step 5107 ends the routine. If not converged, then the residual matrix R is passed 5108 to the non-linear solver for S, such that matrix R is further minimized to provide improved estimates for S. The routine is then iterated until convergence. Optionally, a step 5109 includes applying a least square minimization criterion to either solving steps 5103,5104 for matrices $\hat{S}$ and/or $\hat{A}$.

Another exemplary method 5200 (FIG. 5D) is similar to method 5100 but the initial matrix $\hat{S}_{initial}$ is employed directed to solve for an estimated matrix $\hat{A}$. The method 5200 includes a start prompt 5201 to launch the global analysis method; a step 5202 of constructing initial matrix $\hat{S}_{initial}$ from estimated non-linear term; a step 5203 of linearly solving for an estimated matrix $\hat{A}$ using provided matrix $\hat{S}_{initial}$; a step 5204 of computing a residual matrix R (e.g., using any useful method herein, such as Eqs. 9a, 9b, 21, 23, 24a, 25a, and/or 25b); and a convergence decision step 5205. If converged, then a stopping step 5206 ends the routine. If not converged, then the residual matrix R is passed 5207 to the non-linear solver for S, thereby allowing for a step 5208 of non-linearly solving for an estimated matrix $\hat{S}$ by further minimizing matrix R. The routine is then iterated until convergence. Optionally, steps 5209,5210 include applying a least square minimization criterion to either solving steps 5203,5208 for matrices $\hat{S}$ and/or $\hat{A}$. Additional modifications to any of these routines, in light of the methods and steps disclosed herein, would be apparent to a skilled artisan.

Data Compression

The data matrix D can be compressed in any useful manner. As described herein, matrix D is represented by a multidimensional data space. Depending on the size of each image (a×b, a×b×c, or m) and the n channels of images, the size of the data matrix D can be substantial, i.e., a m×n matrix. In addition, matrix manipulation of such large matrices, in order to arrive at desired solutions for matrices S and A, can be time-consuming. Thus, reducing the size of matrix D can be helpful for computational purposes, but such compression techniques should not arbitrarily remove potentially important data.

Figure 6A:
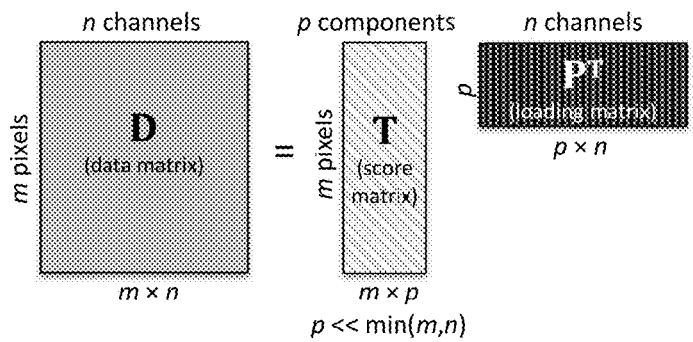
FIG. 6A-6C shows graphic representations of principal component analysis (PCA) for compression of the data matrix D. Provided are a PCA model for matrix D (FIG. 6A); application of the least squares criterion to the data matrix D in order to obtain estimated matrices P and T (FIG. 6B); and a relationship between matrices T and P for the PCA model and matrices S and A (or the least square approximations of matrices S and A) for the analytical model of matrix D (FIG. 6C).
Figure 6B:
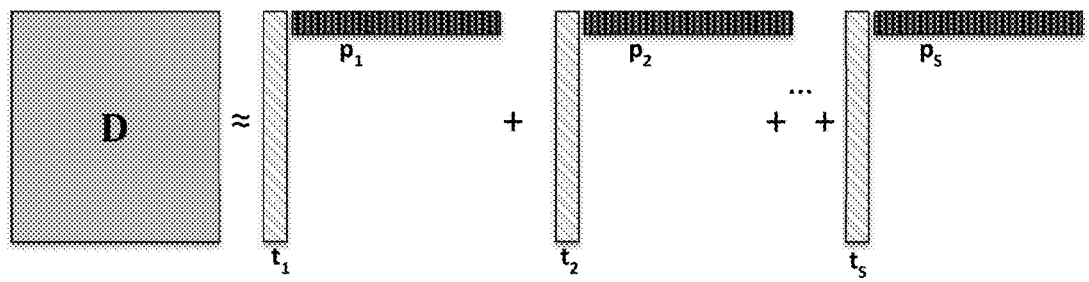
Figure 6C:
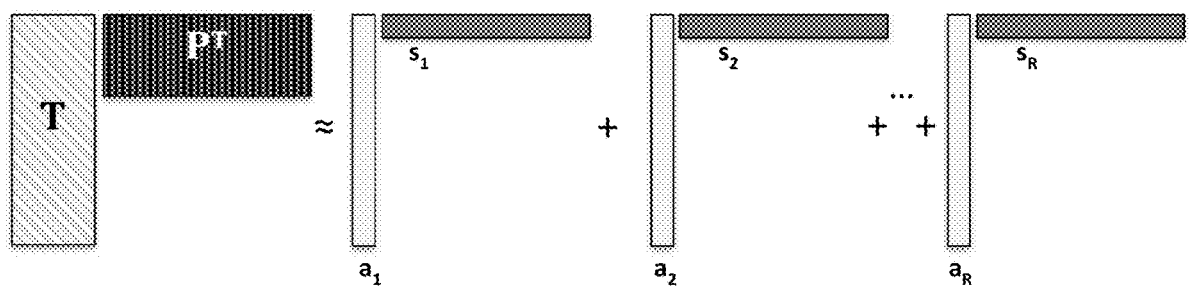

In one instance, principal component analysis (PCA) is employed to compress matrix D. Using PCA, matrix D can be characterized by a single direction (or a first principal component $PC_1$) that maximally accounts for variance in the data. To more fully describe the data, additional principal components can be identified (e.g., $PC_2$, $PC_3$, . . . , $PC_p$, where p is an integer). Each principal component is orthogonal to any other principal component. In addition, each successive principal component possesses a variance of successively lower quantity (i.e., variance of $PC_1$>variance of $PC_2$>variance of $PC_3$, etc.). Typically, the first few principal components contain the chemical information of interest. The remaining principal components generally contain noise or other artifacts. Thus, if the p number of principal components adequately describes the underlying data, then the data matrix D can represented as follows:

$$D=TP^T, \qquad (Eq.\ 11)$$

where D is an m×n data matrix, T is an m×p matrix having mutually orthogonal columns, and P is an n×p matrix having mutually orthonormal columns; superscript $^T$ indicates a matrix transpose; and each of m, n, and p is an integer of 1 or more. Matrix T is conventionally called the score matrix, and matrix P is conventionally called the loading matrix. This PCA model, as well as least square approximations of this model, can be shown graphically (FIG. 6A-6C).

The expression in Eq. 11 represents the data matrix D as a combination of the score matrix T and the loading matrix P. If dimension p is significantly less than both m and n (e.g., p«min(m, n)), then the data matrix can be compressed by being represented by matrices T and P having this dimension p. As shown in FIG. 6C, data matrix D is compressed as matrices A and S, or least squares approximations of A and S, can be expressed as a score matrix T and loading matrix P having a dimension p«min(m, n).

Any useful methodology can be employed to solve the PCA problem in Eq. 11. In one instance, eigenanalysis of the data matrix D, the covariance matrix $D^TD$, or the association matrix $DD^T$ is employed. For example, eigenanalysis of the covariance matrix in conjunction with the compressed expression for D (e.g., Eq. 11) can be expressed as follows:

$$D^TD=(TP^T)^TTP^T=PT^TTP^T=P(T^TT)P^T \qquad (Eq.\ 12)$$

where $T^TT$ is a diagonal p×p matrix that can be optionally solved first in Eq. 12. Performing the calculation of this p×p diagonal matrix, prior to performing matrix multiplication with n×p matrix P and p×n matrix $P^T$, can be desirable, especially as p is generally less than n.

By solving the eigenproblem of Eq. 12, solutions for matrix P can be obtained. After obtaining the loading matrix P, the score matrix T can be obtained as follows:

$$T=DP, \qquad (Eq.\ 13)$$

which can be obtained by re-arranging Eq. 11.

Singular value decomposition (SVD) can be used in conjunction with eigenanalysis to solve Eq. 11. For instance, SVD decomposes D into three matrices:

$$D=U\Delta V^T, \qquad (Eq.\ 14)$$

where U is an m×m orthogonal matrix containing left singular vectors, V is an n×n orthogonal matrix containing right singular vectors, and $\Delta$ is an m×n diagonal matrix with singular values placed along the diagonal. Singular values and corresponding vectors are ordered within these matrices according to their significance.

By comparing Eqs. 11 and 14, PCA analysis can be performed with the following expressions:

$$P=V_p, \text{ and} \qquad (Eq.\ 15a)$$

$$T=(U\Delta)_p=DP \qquad (Eq.\ 15b)$$

where subscript p indicates that only the first p columns of the respective matrices are retained. Furthermore, solutions for V can be obtained by applying eigenanalysis of D as follows:

$$D^TD=(U\Delta V^T)^T(U\Delta V^T)=V\Delta^2V^T, \qquad (Eq.\ 15c)$$

where this eigenvalue problem shows that the right singular vectors V can be obtained as eigenvectors of $D^TD$ and that the squares of the singular values $\Delta^2$ can be obtained as eigenvalues of $D^TD$. Thus, solving Eq. 15c provides V, where the first p components of V can be employed as $V_p$, which in turn provides P according to Eq. 15a. Finally, T can be determined according to Eq. 15b.

Additional methods for principal component analysis (e.g., SVD, eigenvalue decomposition (EVD), an arbitrary f-component factor model, etc.) are described in U.S. Pat. Nos. 6,584,413, 6,675,106, 7,283,684 and 7,400,772, which is incorporated herein by reference in its entirety. Algorithms for implementing SVD and EVD, as well as other PCA algorithms, are described in Wu W et al., "The kernel PCA algorithms for wide data. Part I: theory and algorithms," *Chemom. Intell. Lab. Sys.* 1997; 36:165-72, which is incorporated herein by reference in its entirety.

Figure 9A:
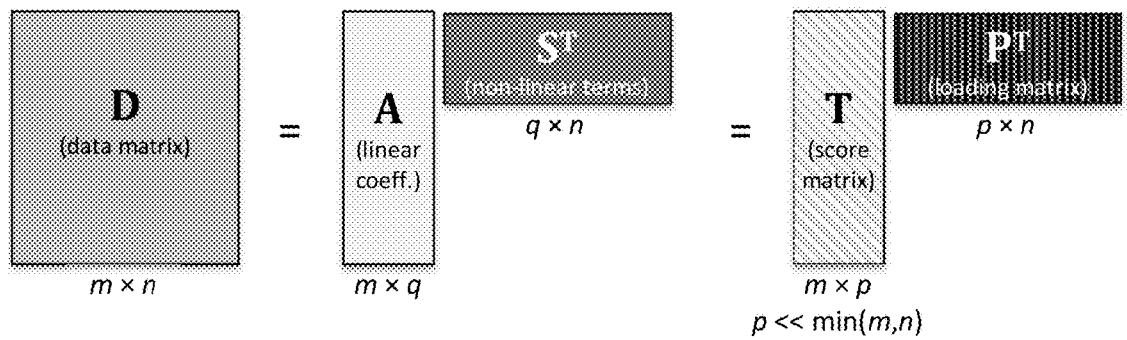
FIG. 9A-9F shows graphic representations of a compressed data matrix D. Provided are a relationship between matrices T and P for the PCA model and matrices S and A for the analytical model of matrix D (FIG. 9A); a definition of an estimator matrix Ã and a least square approximation of matrices S and Ã (FIG. 9B); a relationship between matrices A, T, and Ã (FIG. 9C); and a representation of a score matrix T in terms of matrices D and P (FIG. 9D). Also provided are an exemplary computer-implemented method 900 for compressing data and performing global analysis on compressed data (FIG. 9E); and a second non-limiting method 9000 that employs an estimator matrix Ã (FIG. 9F).
Figure 9B:
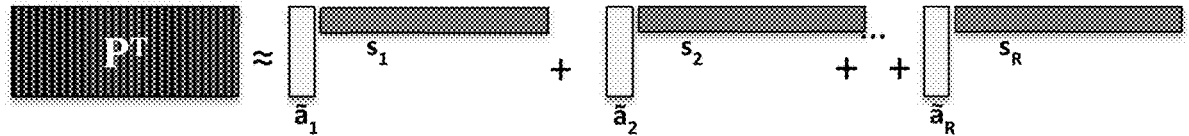
Figure 9C:
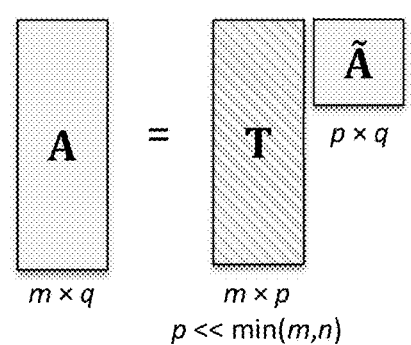
Figure 9D:
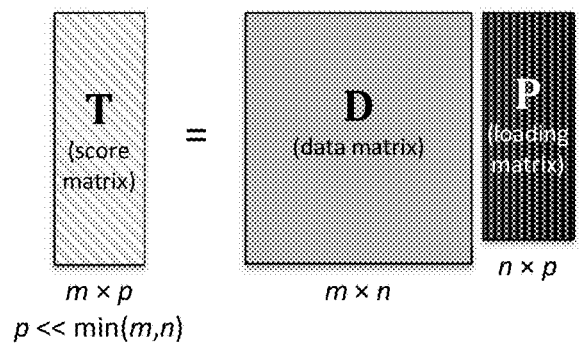

Furthermore, global analysis can be performed by analyzing the following expression:

$$D = TP^T = AS^T, \qquad \text{(Eq. 16)}$$

which is also depicted graphically in FIG. 9A. In one instance, matrices P and T are obtained by eigenanalysis or any other useful method, matrix S is obtained by non-linearly solving, and matrix A is obtained by the following expression construed from Eq. 16:

$$A = TP^TS(S^TS)^{-1} = T(P^TS)(S^TS)^{-1} \qquad \text{(Eq. 17)}$$

In particular embodiments, the expression $P^TS$ is optionally solved first in Eq. 17. Performing this calculation provides a p×q matrix, where p and q, independently, are generally less than m and n.

Figure 7:
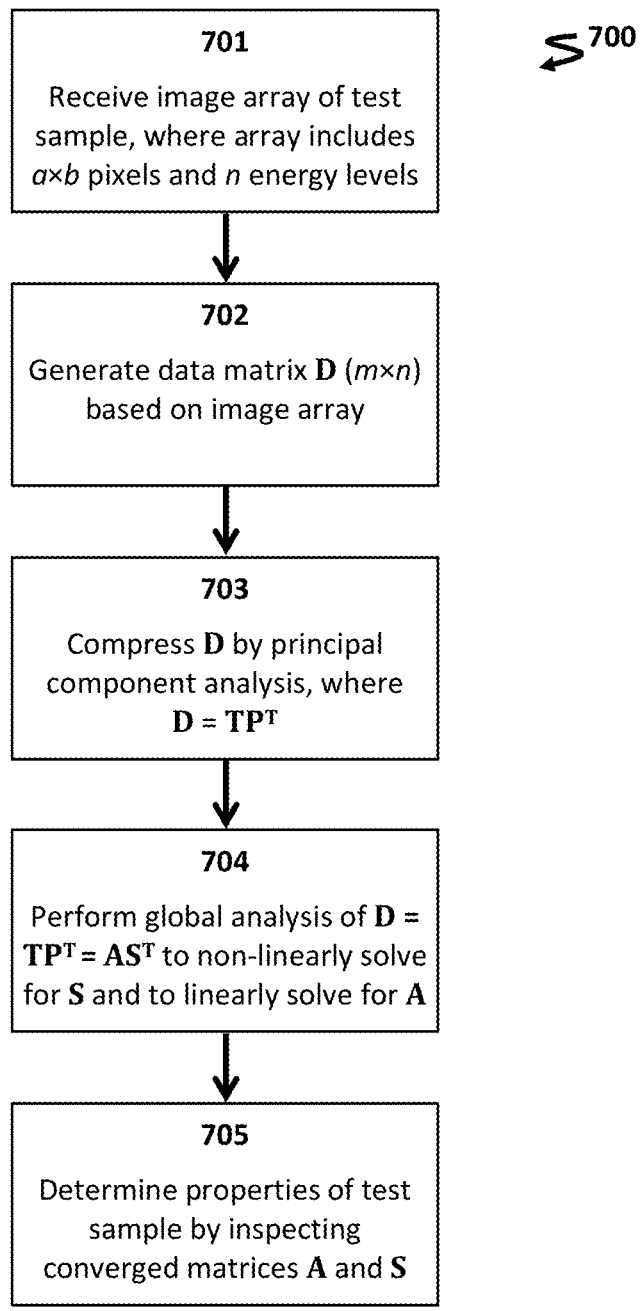
FIG. 7 shows an exemplary method 700 for global analysis of compressed data for a chemical test sample.

The PCA model can be used jointly with the analytical model for data in any useful global analysis method (e.g., any global analysis method described herein). One exemplary method 700 combines a global analysis method with a PCA model. As seen in FIG. 7, the global analysis method 700 includes numerous steps, including a step 701 of receiving an image array of a test sample, where array includes a plurality of images. Each image has a×b pixels, and one image is captured for each n energy levels, thereby providing n number of images. The next step 702 includes generating a data matrix D (m×n) based on the image array by unfolding, as described herein, where m is a times b. A third step 703 includes compressing data matrix D by principal component analysis, where $D = TP^T$ (Eq. 11).

A further step 704 includes performing global analysis on the compressed data matrix, as described herein, of $D = TP^T = AS^T$ (Eq. 16). This step 704 can be performed in order to (i) solve for the loading matrix P (e.g., using Eqs. 11, 12, 15a, or 15c), (ii) solve for the score matrix T (e.g. using Eqs. 13 or 15b), (iii) non-linearly solve for matrix S, and (iv) linearly solve for matrix A (e.g., using Eq. 17), where (i), (ii), (iii), and (iv) can be performed in any order or at the same time. For instance, steps (i) and (iii) can be performed in any order or at the same time. Step (ii), which benefits from a solution obtained in step (i), is generally but not always performed after step (i). However, step (ii) can be performed before or after step (iii). Finally, step (iv), which benefits from a solution obtained in steps (i), (ii), and (iii), is generally but not always performed after these steps.

The final step 705 includes determining one or more properties of test sample (e.g., chemical properties, bonding properties, etc.) by inspecting converged matrices A and S (e.g., including converted versions of matrices A and S). Optionally, the global analysis step 704 includes applying a least squares criterion to A and/or S. Each of these steps can be performed using a computer, a processor, a memory, a program code, etc.

Figure 8:
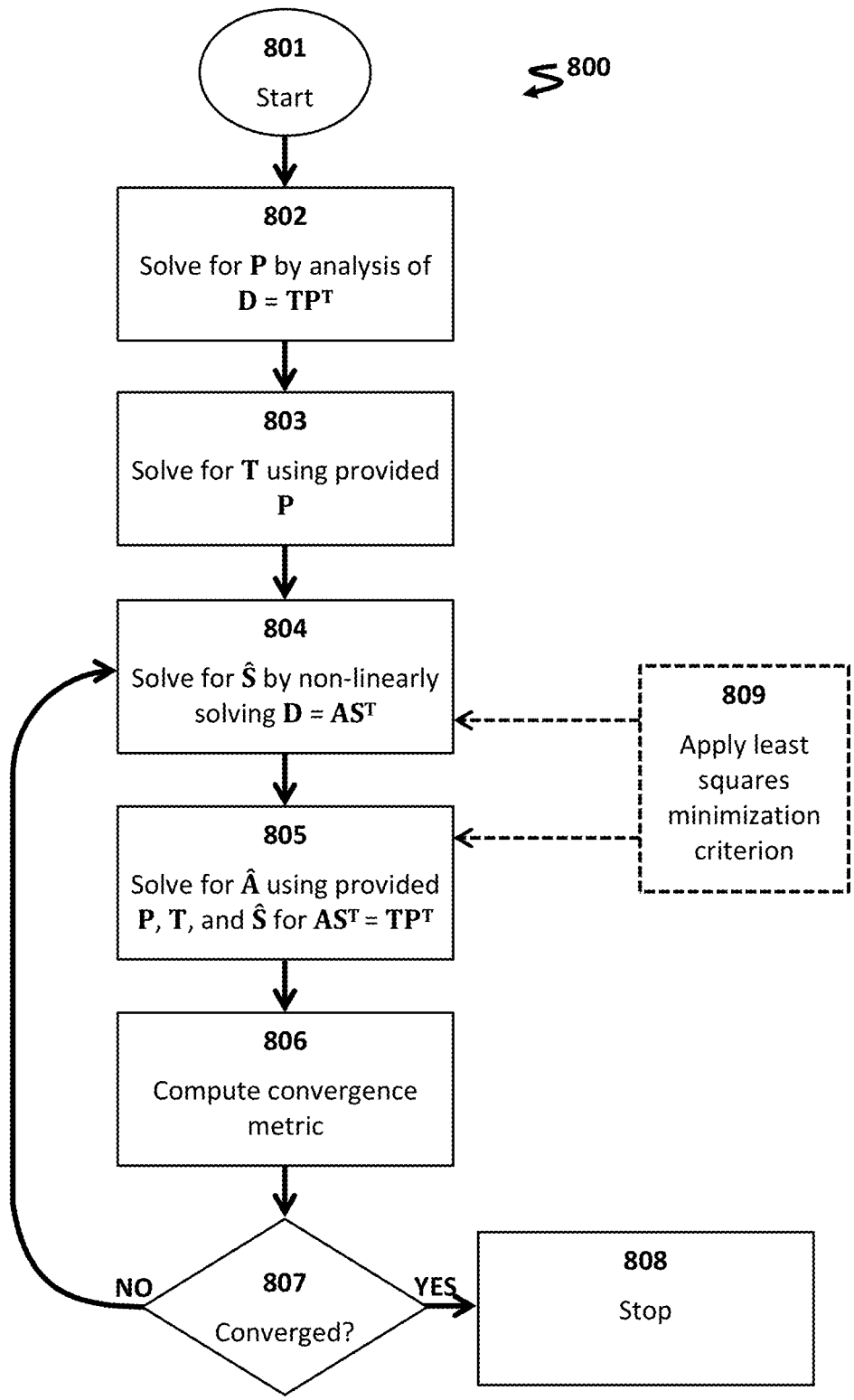
FIG. 8 shows an exemplary computer-implemented method 800 for compressing data and performing global analysis on the compressed data.

The PCA model and analytical model can be performed in any useful manner, such as by using a computer (e.g., as described herein). Any of the global analysis methods herein can be modified to include PCA compression. For instance, an exemplary computer-implemented method 800 (FIG. 8) includes a routine of steps capable of being programmed in any useful computer code language.

The method 800 includes a start prompt 801 to launch the global analysis method; a step 802 of solving for the loading matrix P by analysis of $D = TP^T$; a step 803 of solving for the score matrix T using provided loading matrix P (e.g., by using Eq. 13); a step 804 of solving for an estimated matrix $\hat{S}$ by non-linearly solving $D = AS^T$; a step 805 of solving for an estimated matrix $\hat{A}$ using the provided loading matrix P, the provided score matrix T, and the estimated matrix $\hat{S}$ as S in the following equation $AS^T = TP^T$ or any other useful equation described herein (e.g., Eq. 17); a step 806 of computing a convergence metric; and a decision step 807 of determining whether the convergence metric meets the convergence criterion. If converged, then a stopping step 808 ends the routine. If not converged, then the routine is iterated until convergence. Optionally, a step 809 includes applying a least square minimization criterion to either solving steps 804,805 for matrices $\hat{S}$ and/or $\hat{A}$. As described herein, step In another instance, the loading matrix P can be defined by an estimator matrix $\tilde{A}$ for matrix A. As seen in FIG. 9A, recall that the model includes an analytical model for the data matrix D, where this analytical model includes matrix A of linear terms and matrix S of non-linear terms. By employing data compression, the PCA model provides a score matrix T and a loading matrix P, which allows us to define P as follows:

$$P^T = \tilde{A}S^T \text{ and} \qquad \text{(Eq. 18)}$$

$$A = T\tilde{A}, \qquad \text{(Eq. 19)}$$

where estimator matrix $\tilde{A}$ is a p×q matrix. FIG. 9A-9D shows the relevant matrices and expressions in a graphical manner.

Using these expressions, the loading matrix P can be used in a global analysis in order to determine solutions for the estimator matrix $\tilde{A}$, where solutions for this minimized matrix can be obtained in any useful manner (e.g., by least squares). In one instance, $\tilde{A}$ can be obtained using least squares, which can be formally described as follows:

$$\tilde{A}^{min} \|P^T - \tilde{A}S^T\|_F^2. \qquad \text{(Eq. 20)}$$

The non-linear terms can be solved to obtain estimated matrix $\hat{S}$, where this step can be performed before or after obtaining the estimator matrix $\tilde{A}$.

Estimates for matrix S and the estimator matrix $\tilde{A}$ can be obtained in an iterative manner until convergence, which can be determined by any useful residual matrix R. In instance, the residual matrix is determined as follows:

$$R = \hat{\tilde{A}} - D\hat{S}(\hat{S}^T\hat{S})^{-1}, \qquad \text{(Eq. 21)}$$

where $\hat{\tilde{A}}$ is an estimated estimator matrix and $\hat{S}$ is any useful estimated matrix for S. To ensure that the estimated matrices $\hat{S}$ and $\hat{\tilde{A}}$ appropriately model the real data, the solving steps for matrices S and $\tilde{A}$ (performed in any useful order) can be iterated as needed until convergence. Iterations can include estimating estimator matrix $\hat{\tilde{A}}$ and then matrix $\hat{S}$, or vice versa. After convergence, estimator matrix $\tilde{A}$ can be converted to matrix A in any useful manner (e.g., by using Eq. 13 to obtain matrix T and Eq. 19 to get matrix A).

Figure 9E:
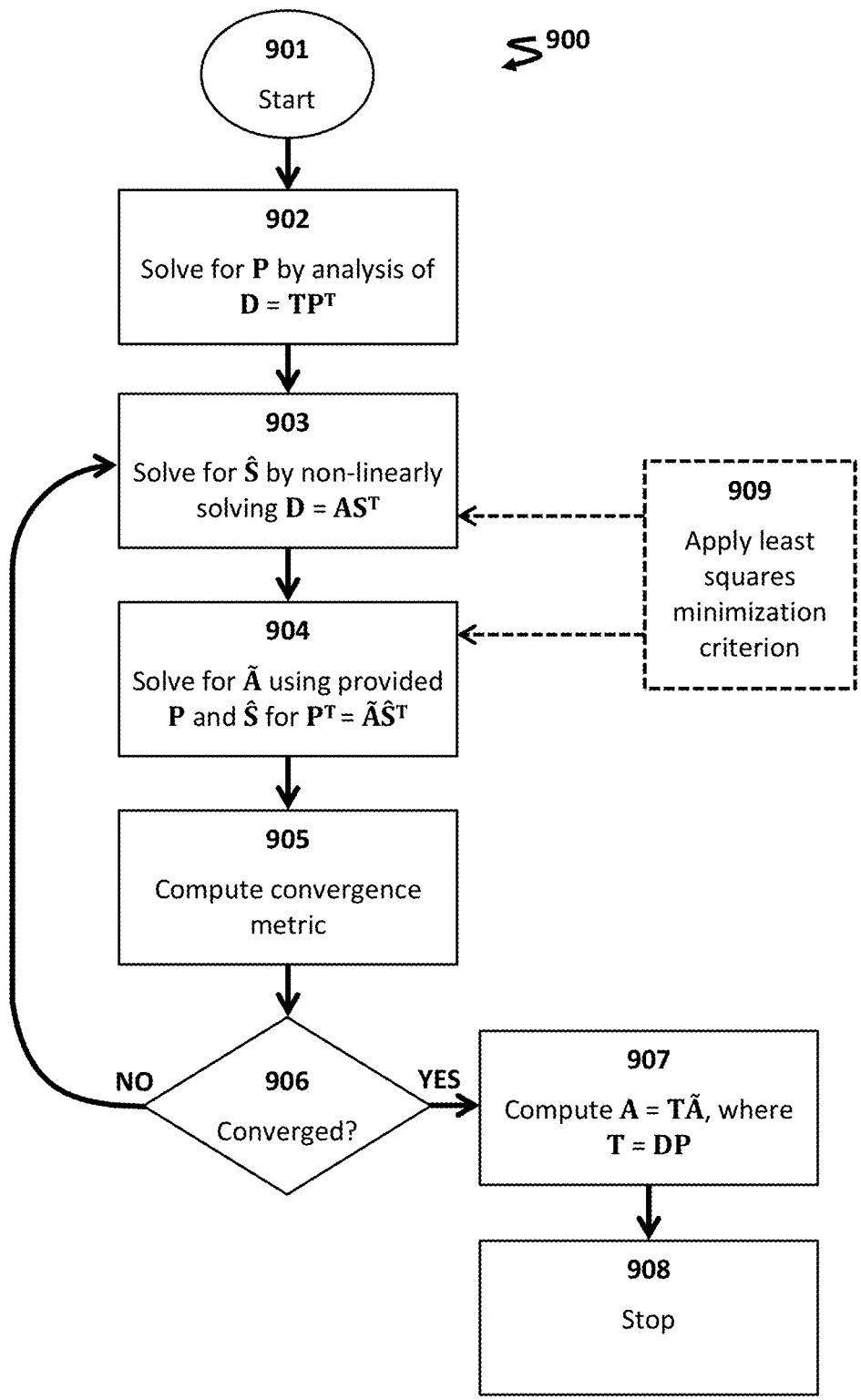
Figure 9F:
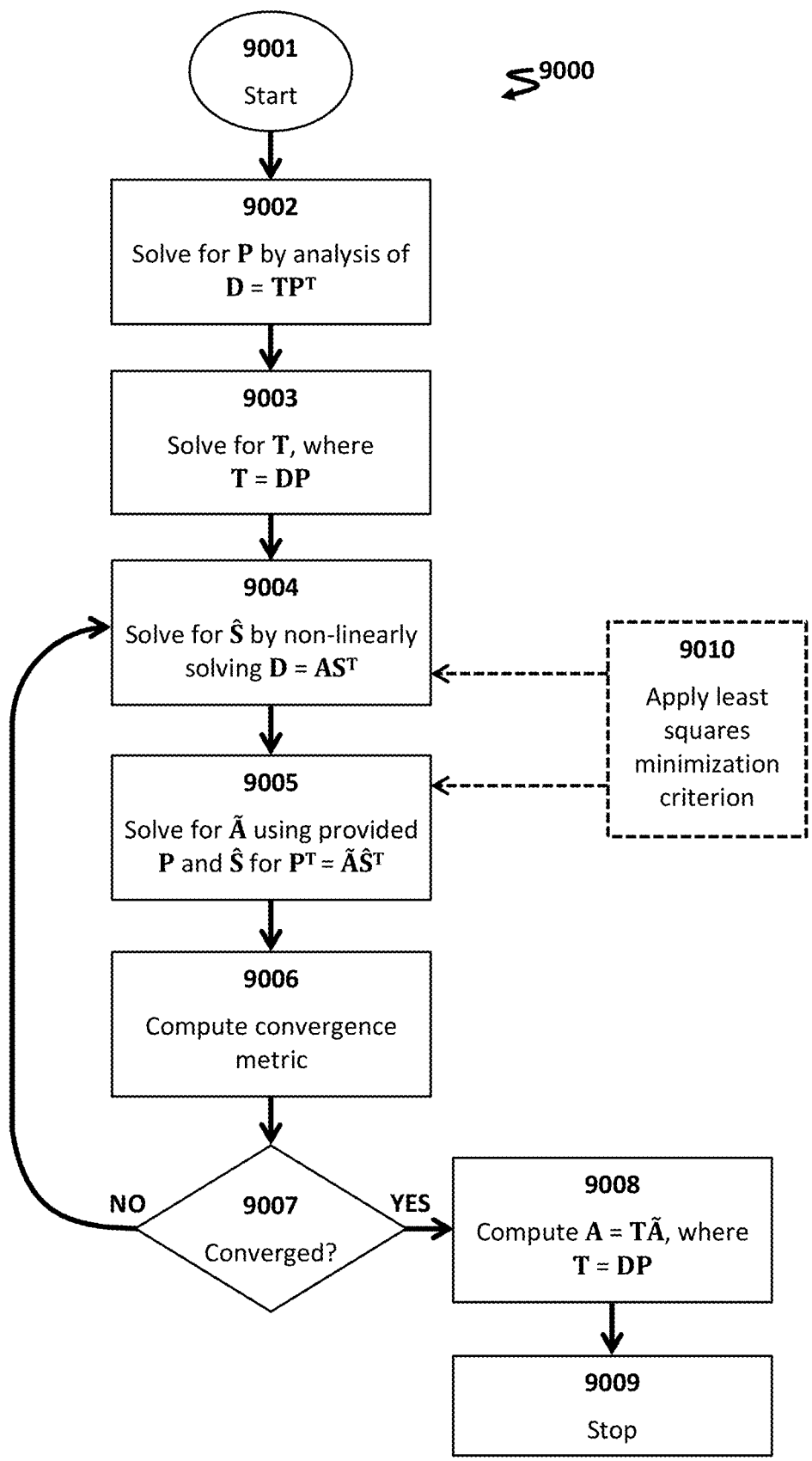

FIG. 9E-9F shows exemplary computer-implemented methods 900,9000 including a routine of steps employing the estimator matrix $\tilde{A}$ and capable of being programmed in any useful computer code language. One exemplary method 900 (FIG. 9E) includes a start prompt 901 to launch the global analysis method; a step 902 of solving for the loading matrix P by analysis of $D=TP^T$; a step 903 of solving for an estimated matrix $\hat{S}$ by non-linearly solving $D=AS^T$; a step 904 of solving for an estimator matrix $\tilde{A}$ using the provided loading matrix P and the provided estimated matrix $\hat{S}$ as S in the following equation $P^T=\tilde{A}S^T$ or any other useful equation described herein; a step 905 of computing a convergence metric; and a decision step 906 of determining whether the convergence metric meets the convergence criterion. If converged, then the method can proceed to a calculation step 907 of computing the matrix A using the provided estimator matrix $\tilde{A}$ (e.g., using Eq. 19) and the loading matrix P, where matrix P can be used to determine the score matrix T (e.g., using Eq. 13); and then to a stopping step 908 to end the routine. If not converged, then the routine is iterated until convergence. Optionally, a step 909 includes applying a least square minimization criterion to either solving steps 903,904 for matrices $\hat{S}$ and/or $\tilde{A}$.

Another exemplary method 9000 (FIG. 9F) includes calculation of the score matrix T prior to reaching convergence. The method 9000 includes a start prompt 9001 to launch the global analysis method; a step 9002 of solving for the loading matrix P by analysis of $D=TP^T$; a step 9003 of solving for the score matrix T by analysis of $T=DP$; a step 9004 of solving for an estimated matrix $\hat{S}$ by non-linearly solving $D=AS^T$; a step 9005 of solving for an estimator matrix $\tilde{A}$ using the provided loading matrix P and the provided estimated matrix $\hat{S}$ as S in the following equation $P^T=\tilde{A}S^T$ or any other useful equation described herein; a step 9006 of computing a convergence metric; and a decision step 9007 of determining whether the convergence metric meets the convergence criterion. If converged, then the method can proceed to a calculation step 9008 of computing the matrix A using the provided estimator matrix $\tilde{A}$ and the provided score matrix T (e.g., using Eq. 19); and then to a stopping step 9009 to end the routine. If not converged, then the routine is iterated until convergence. Optionally, a step 9010 includes applying a least square minimization criterion to either solving steps 9004,9005 for matrices $\hat{S}$ and/or $\tilde{A}$.

Convergence and Residual Matrices Solutions for matrices S or A generally include an iterative process, in which i number of steps is repeated until convergence is reached. Convergence can be determined in any useful manner. For instance, the extent of convergence can be determined by calculating a residual matrix R, which represents any data in the data matrix D that is not accounted by estimated matrices for A, S, T, or P:

$$D=AS^T+R \text{ or} \qquad \text{(Eq. 22a)}$$

$$D=T\tilde{A}S^T+R \text{ or} \qquad \text{(Eq. 22a)}$$

$$D=TP^T+R. \qquad \text{(Eq. 22b)}$$

In essence, residual matrix R accounts for any error between the real data and the model:

$$R=D-\hat{D}, \qquad \text{(Eq. 23)}$$

where D is the real data matrix and $\hat{D}$ is a reconstructed data matrix obtained from any matrices A, S, T, and P obtained by global analysis (e.g., estimated matrices of any of these).

The measure of acceptable error is the convergence criterion, which can be determined in any useful manner. In terms of the residual matrix R, a convergence criterion can include a sum of the squares of the residual matrix or a sum of the square of the two-norm of the difference vector. In one instance, the convergence criterion is a sum of the squares of the residual matrix SSR determined as follows:

$$SSR=\min\|R\|_F^2, \qquad \text{(Eq. 22)}$$

where subscript F represents the Frobenius norm and this squared Frobenius norm represents the sum of the squared difference over the entire dataset.

In another example, residuals can be determined according to a reconstructed data matrix $\hat{D}$, as follows:

$$\hat{D}=AS^T \text{ or} \qquad \text{(Eq. 23a)}$$

$$\hat{D}=TP^T, \text{ and} \qquad \text{(Eq. 23b)}$$

$$SSR=\min\|D-\hat{D}\|_F^2, \qquad \text{(Eq. 23c)}$$

in which A, S, T, and P can be any matrices obtained as described herein.

In yet another example, the residual is determined as follows:

$$R=D-AS^T, \text{ and} \qquad \text{(Eq. 24a)}$$

$$SSR=\min\|D-AS^T\|_F^2, \qquad \text{(Eq. 24b)}$$

where D is the real data matrix, A and S can be any matrices obtained as described herein, and $r_j$ is a vector of the residual matrix R, where the trace of a matrix is the sum of its diagonal components.

In other examples, residuals can be determined by individual matrices that represent the entire data matrix D, such by individual matrices A or S. Thus, residuals can be determined as follows:

$$R=S_{i+1}-S_i \text{ or} \qquad \text{(Eq. 25a)}$$

$$R=A_{i+1}-A_i, \text{ and} \qquad \text{(Eq. 25b)}$$

$$SSR=\Sigma(r_j^T r_j), \text{ where } j=1, \ldots, p \text{ or } j=1, \ldots, q. \qquad \text{(Eq. 25c)}$$

In general, asp and q are less than m and n, calculation of the SSR in Eq. 25c can be less intensive computationally, than calculating of the SSR in Eq. 24b.

Convergence can be quantified by the residual matrix R or SSR, as described herein. The convergence criteria can be assessed numerically, such as by setting a convergence criteria to be an SSR value of $10^{-3}$, $10^{-4}$, $10^{-5}$, $10^{-6}$, $10^{-7}$, $10^{-8}$, $10^{-9}$, $10^{-10}$, or any other useful value.

Conversion of Matrices into Spectra or Images As described herein, matrices A and S are obtained after analysis of the data matrix D. In addition, the accuracy of A and S in describing the data is measured to the extent that obtained matrices for A and S converge with D according to Eq. 1. Of course, if compression is employed, then matrices T and P will be obtained.

After convergence, obtained matrices (e.g., A, S, T, and/or P) can be converted into spectra or images that are more readily interpretable. The obtained matrices can be used to provide a reconstructed data matrix $\hat{D}$, as described herein (e.g., Eqs. 23a and 23b).

Conversion can be implemented in any useful manner. In one instance, each of the q factors can be displayed to show its contribution to an image, such as in FIGS. 13, 14A, 14B, and 16. In another instance, each of the q factors can be displayed as a curve obtained with each calculated non-linear and linear term, e.g., such as in FIGS. 12B and 17. In particular, Eq. 1 can be employed using obtained matrices S and A to reconstruct an estimated data matrix $\hat{D}$, which in turn can be folded into spectra or images interpretable by a user. Folding processes can include one or more steps of the unfolding process (e.g., as described herein) that are performed in the reverse order.

EXAMPLES

Example 1: Global Analysis of NEXAFS Images of Nitrile Samples

We investigated the use of NEXAFS in elucidating how a material ages upon exposure to environmental test conditions. In particular, NEXAFS is an interesting spectroscopy technique that provides information about chemical bonds in various types of materials, including organic materials. Spectral data can be interpreted by one or more peak fitting techniques, in which peaks are identified by a particular line shape and intensity that, in turn, can be correlated with known peaks for known chemical bonds. Thus, peak fitting can help elucidate the nature of bonding in polymers. In conventional analysis, peak fitting is performed on a single spectrum. Here, we propose analyzing NEXAFS image arrays in a global analysis manner. By fitting NEXAFS images and multiple spectra simultaneously, we can provide information about the areal extent of chemical bonding in the material, as well as the presence of mixed species.

Figure 10:
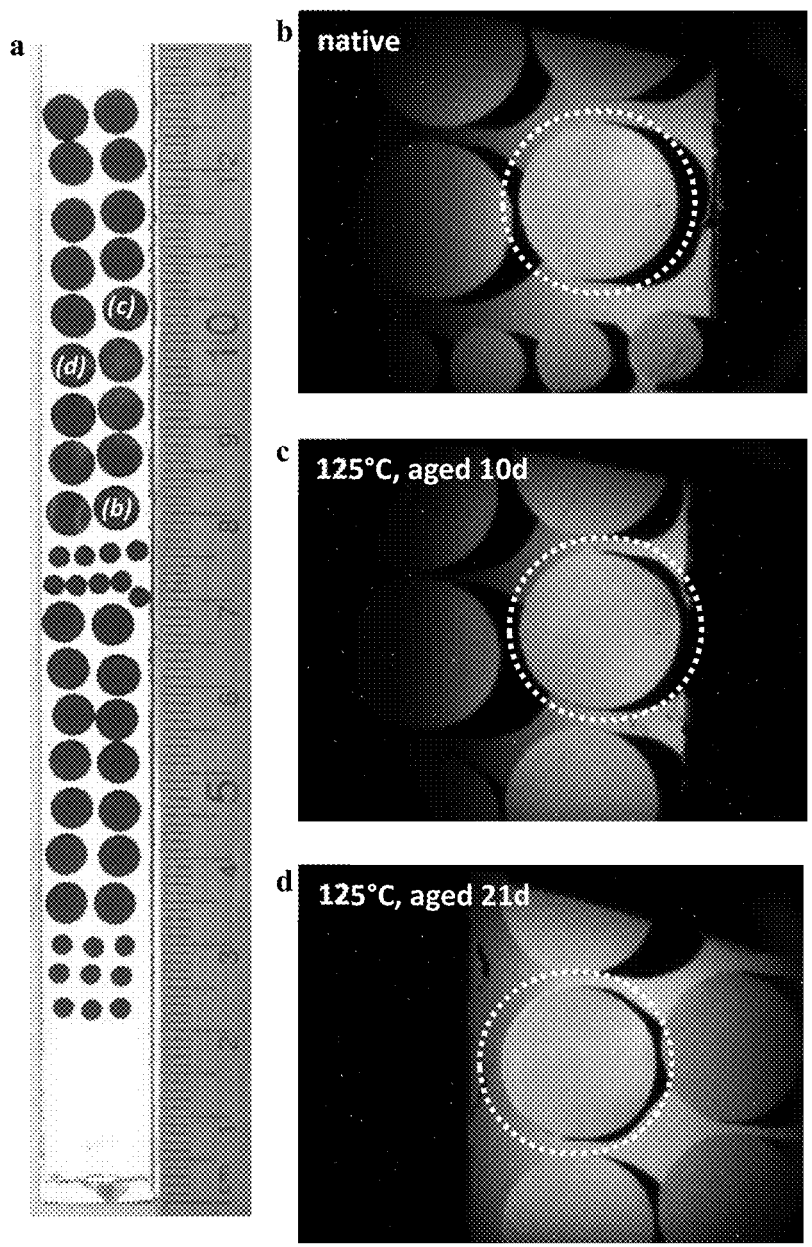
FIG. 10 shows images of nitrile test samples under native and aged conditions. Provided are (a) a photograph of numerous samples under various conditions; (b) a near edge absorption X-ray fine structure (NEXAFS) image for a native nitrile sample that has not been aged (indicted by white outline); (c) a NEXAFS image for a nitrile sample aged for 10 days (10 d) at 125° C.; and (d) a NEXAFS image for a nitrile sample aged for 21 days (21 d) at 125° C. Each image is an integrated image (i.e., an image including intensity data for each energy level).

The test sample included nitrile rubber o-ring gaskets filled with unknown fillers. O-rings were diced into ~1 cm length pieces and then artificially aged under different conditions in air ovens, including 10 days in 125° C. and 21 days in 125° C. Native samples were not aged and employed as controls. After aging, ~1 mm slices were extracted away from the end of each piece and placed onto a sample platen for NEXAFS analysis with double-sided copper tape. Samples were analyzed on the LARIAT imaging NEXAFS end station located at the National Synchrotron Light Source at the Brookhaven National Laboratory. Scans were obtained for energy levels from 270 eV to 348 eV with 0.2 eV per step (391 spectral channels) and acquired at a rate of 1 second per frame, 2 frames per step, at a 50V grid bias. FIG. 10 provides images of the analyzed samples.

Figure 11:
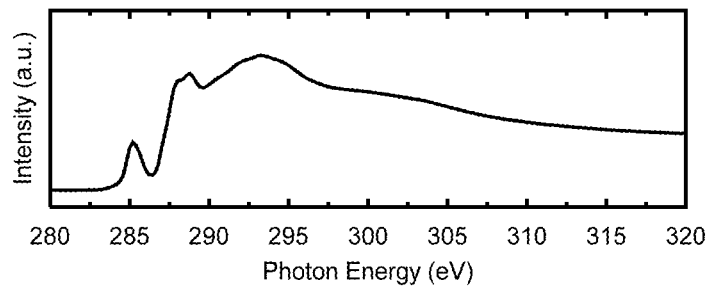
FIG. 11 is a NEXAFS spectrum for a native nitrile sample.

Each individual image was processed to remove outliers, normalized to a baseline intensity, analyzed to determine variance from duplicate frames, and cropped to include only the material or interest. Then, data files were concatenated and processed using the global analysis routine described herein. In particular, 12 factors were employed in this analysis: five symmetrical Voigt peaks, five asymmetrical Voigt peaks, one step function, and one horizontal offset functions. Constraints for symmetrical Voigt peaks required that all have the same peak width and must be at a lower energy than the step function. Constraints for asymmetrical Voigt peaks required that the factors must follow the model in reference and must be at a higher energy than the step function. The step location was based on similar samples noted in the literature (e.g., Dhez O et al., "Calibrated NEXAFS spectra of some common polymers," *J. Electron Spectrosc. Relat. Phenom.* 2003; 128(1):85-96; and Zhou P H et al., "Electronic structure of photo-degraded polypropylene ultrathin films," *Chem. Phys. Lett.* 2008; 465(4-6): 241-4), and image-mode factor intensities were scaled to a common total intensity for all samples. FIG. 11 shows an exemplary NEXAFS spectrum obtained by this analysis of the nitrile sample.

Figure 12A:
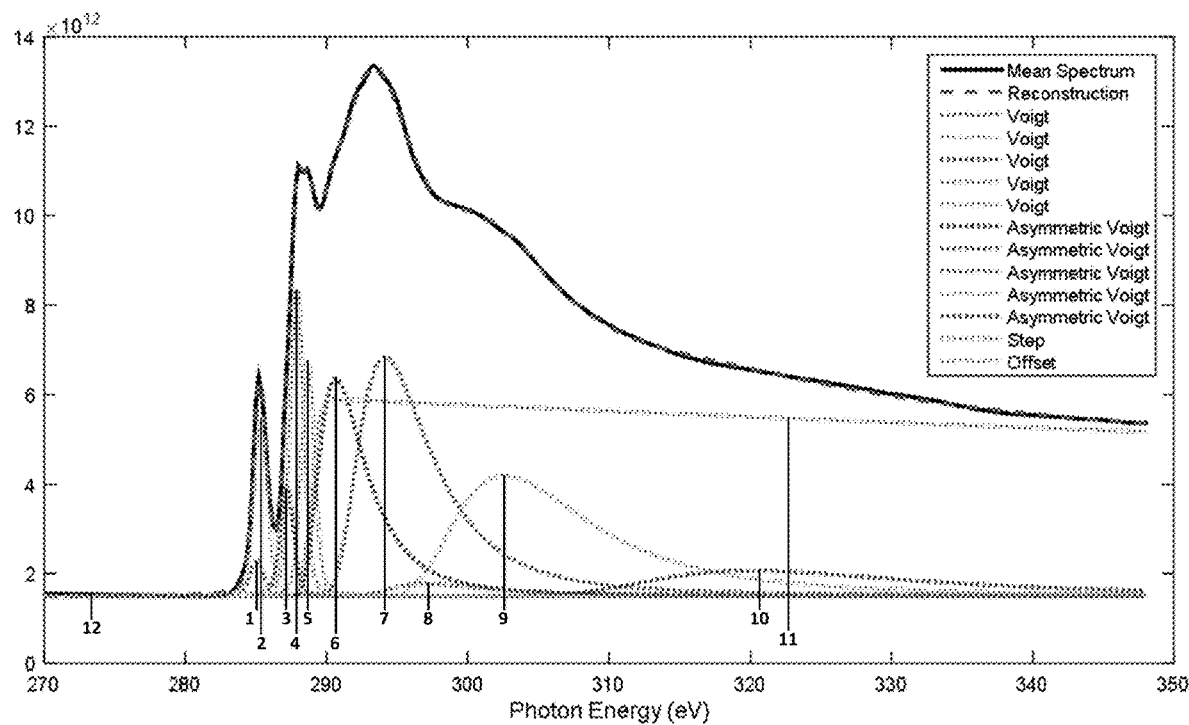
FIG. 12A-12B shows a comparison of the mean NEXAFS spectrum data for the nitrile samples and the fits obtained by global analysis. Provided is a graph showing the overlay of the mean data (black solid line) with a reconstruction of the simulated fits (dashed line), which in turn is a combination of 12 individual fits for 12 different factors (dotted lines) (FIG. 12A). The 12 factors include 5 Voigt fits, 5 asymmetric Voight fits, 1 step fit, and 1 offset. Also provided is a magnified view (FIG. 12B) of the graph for energy levels from about 280 eV to 300 eV, where peaks are labeled with their respective $E_0$ values, i.e., the energy level corresponding to the center position of the peak or step for each factor. Also provided is the chemical structure of the nitrile polymer.
Figure 12B:
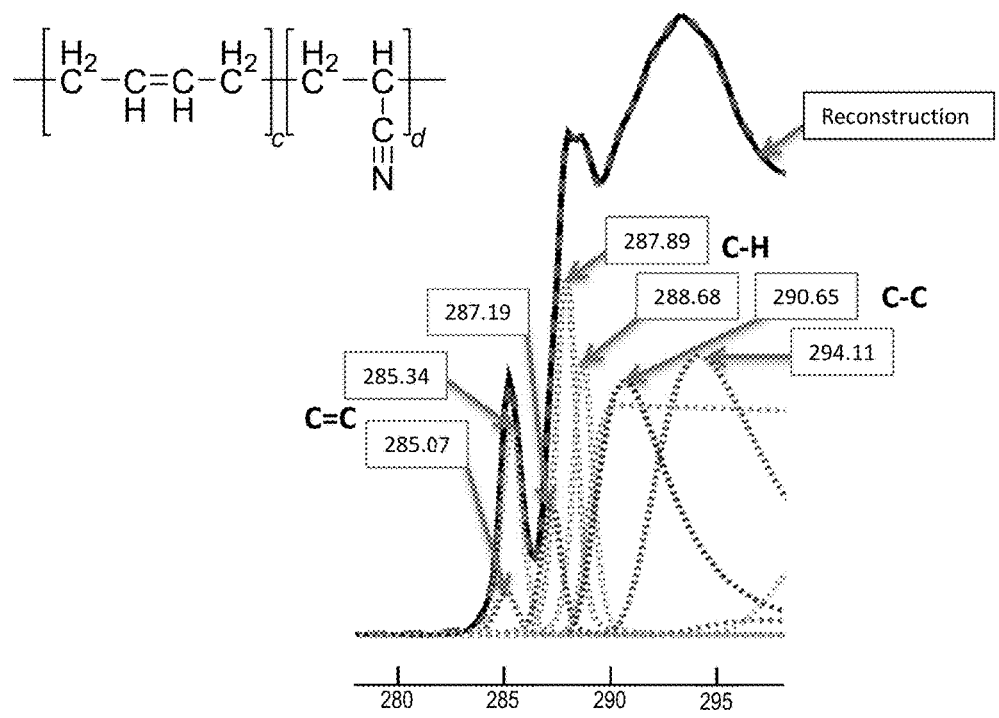
Figure 13A:
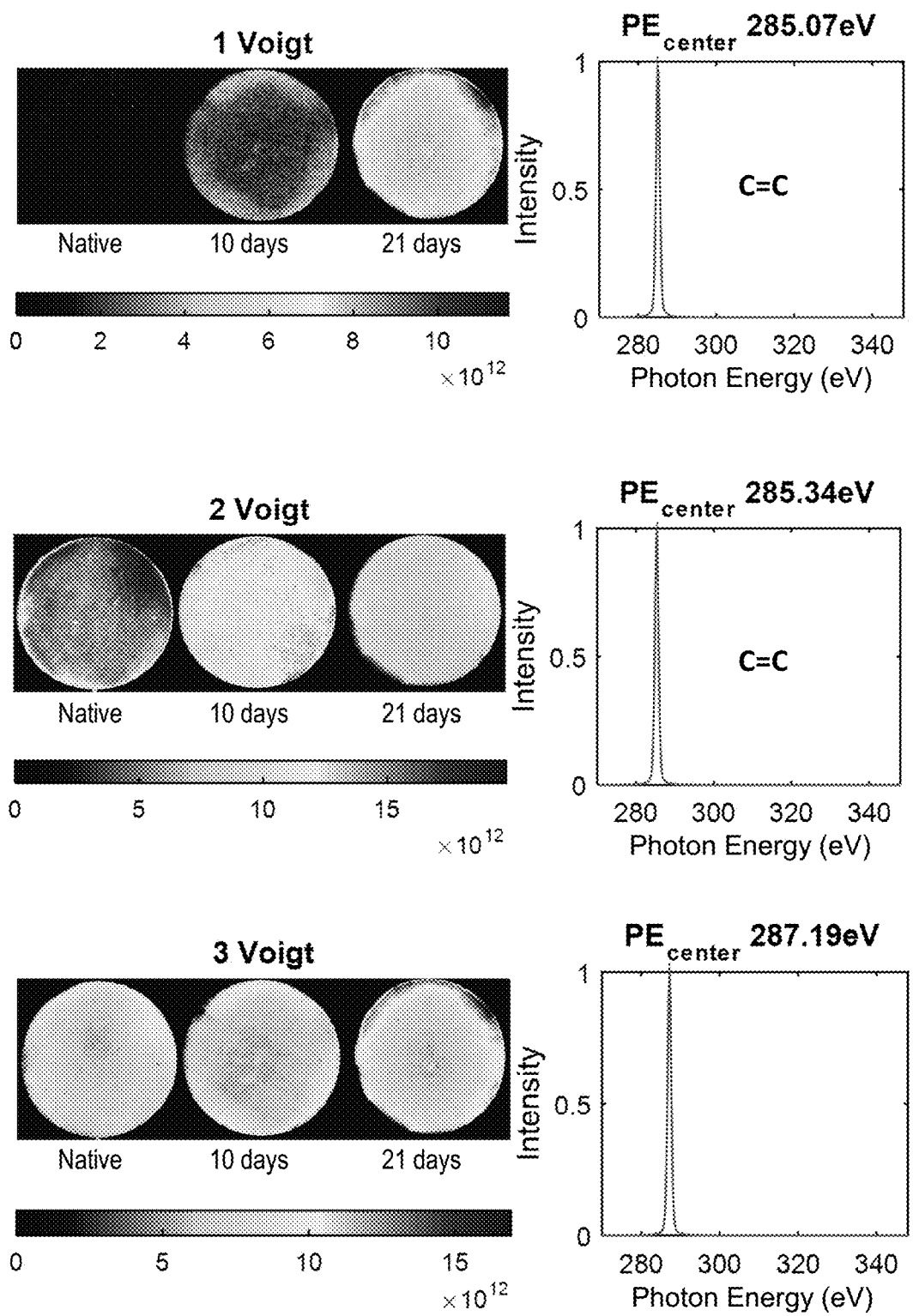
FIG. 13A-13D shows the 12 factors used to characterize native and aged nitrile samples. Provided are (left) reconstructed images that represent each factor (numbered 1 to 12, as shown in FIG. 12A) and (right) a reconstructed spectrum that represents each factor. Image comparisons are shown for the native sample, the aged sample (for 10 days), and another aged sample (for 21 days). Factors include factor 1 (a first Voigt fit with $E_0$ of 285.07 eV, FIG. 13A), factor 2 (a second Voigt fit with $E_0$ of 285.34 eV, FIG. 13A), factor 3 (a third Voigt fit with $E_0$ of 287.19 eV, FIG. 13A), factor 4 (a fourth Voigt fit with $E_0$ of 287.89 eV, FIG. 13B), factor 5 (a fifth Voigt fit with $E_0$ of 288.68 eV, FIG. 13B), factor 6 (a first asymmetric Voigt fit with $E_0$ of 290.65 eV, FIG. 13B), factor 7 (a second asymmetric Voigt fit with $E_0$ of 294.12 eV, FIG. 13C), factor 8 (a third asymmetric Voigt fit with $E_0$ of 297.04 eV, FIG. 13C), factor 9 (a fourth asymmetric Voigt fit with $E_0$ of 302.62 eV, FIG. 13C), factor 10 (a fifth asymmetric Voigt fit with $E_0$ of 320.00 eV, FIG. 13D), factor 11 (a step fit with $E_0$ of 288.91 eV, FIG. 13D), and factor 12 (an offset, FIG. 13D), where $E_0$ (or PE center) indicates the center position of the peak or step.
Figure 13B:
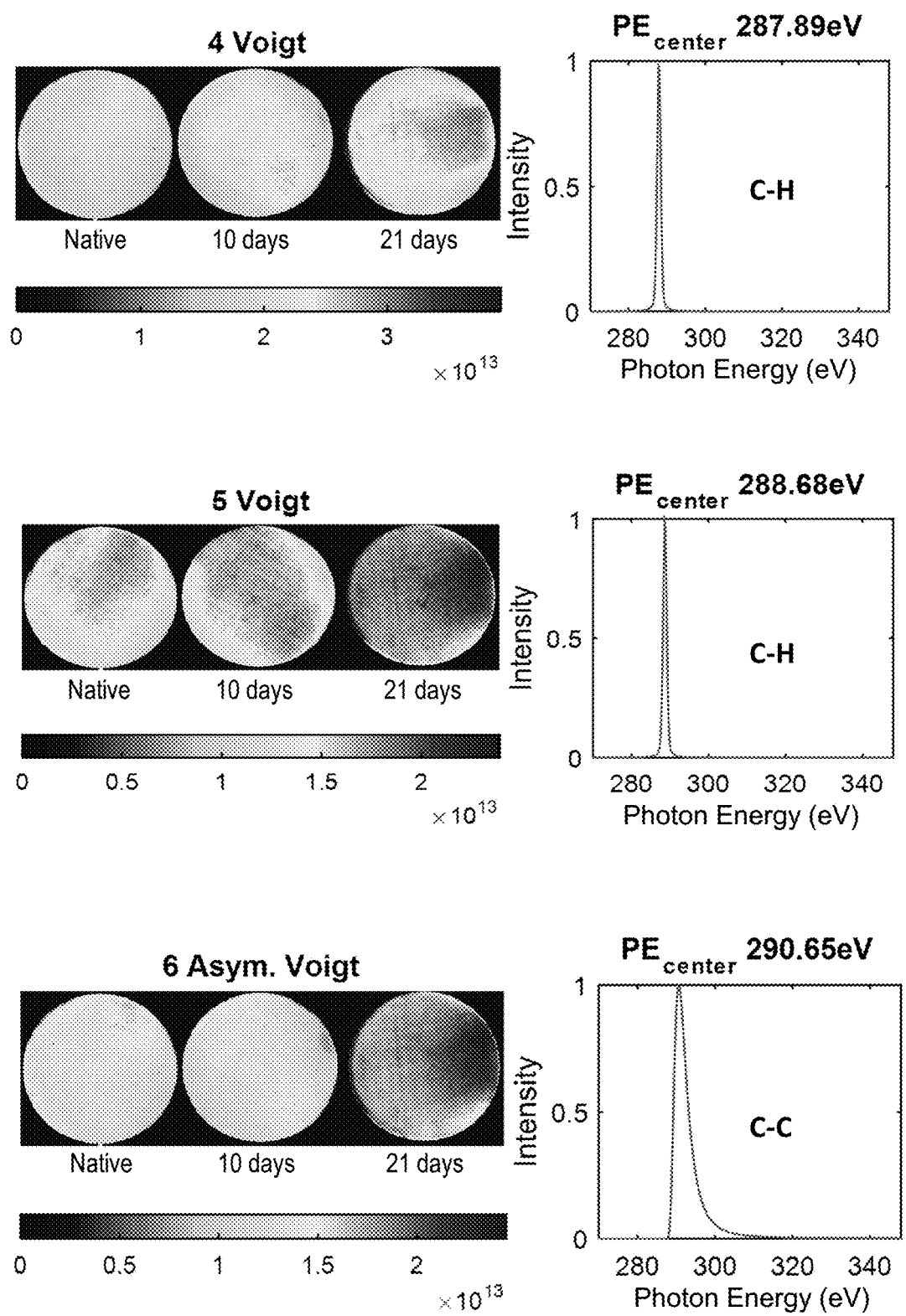
Figure 13C:
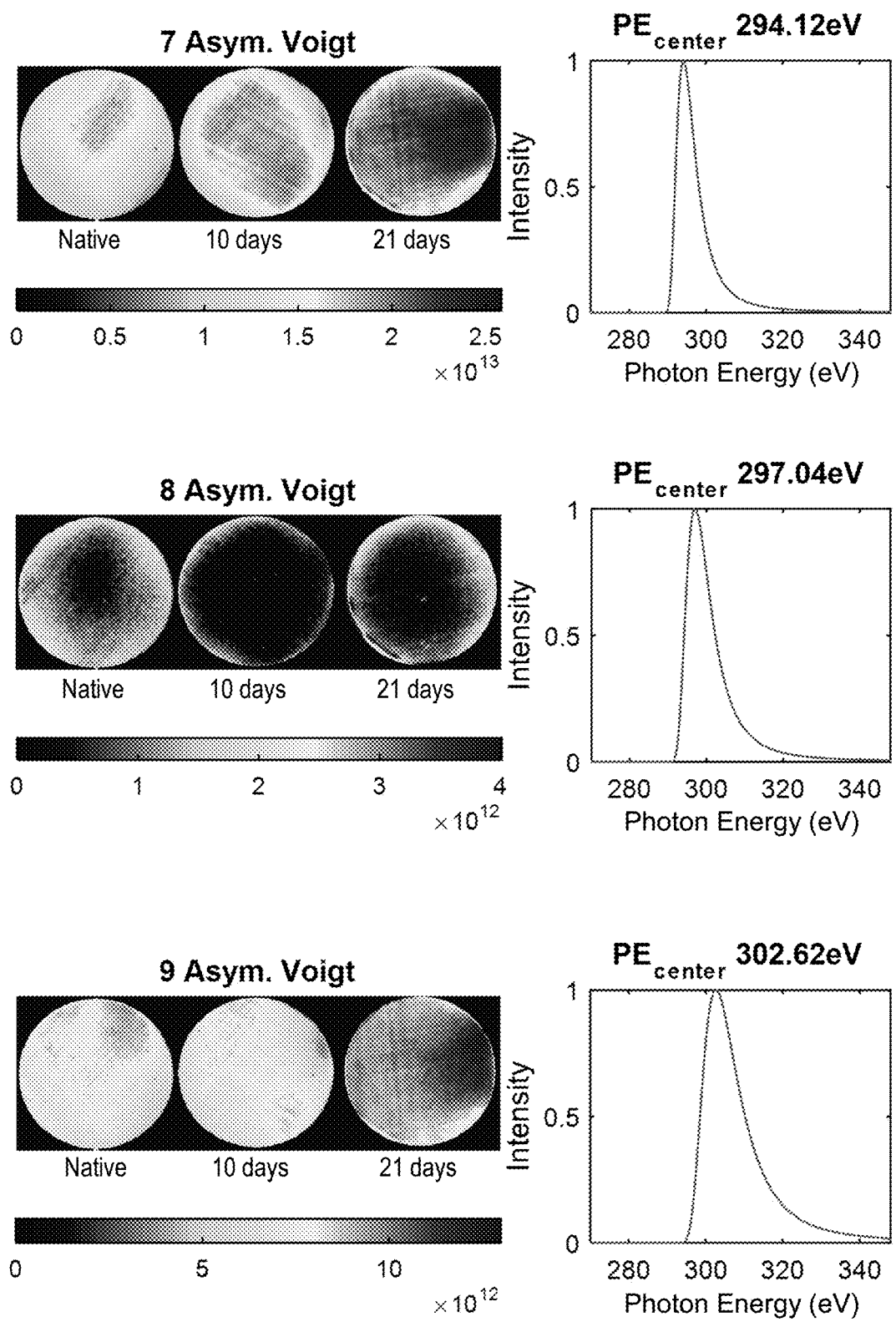
Figure 13D:
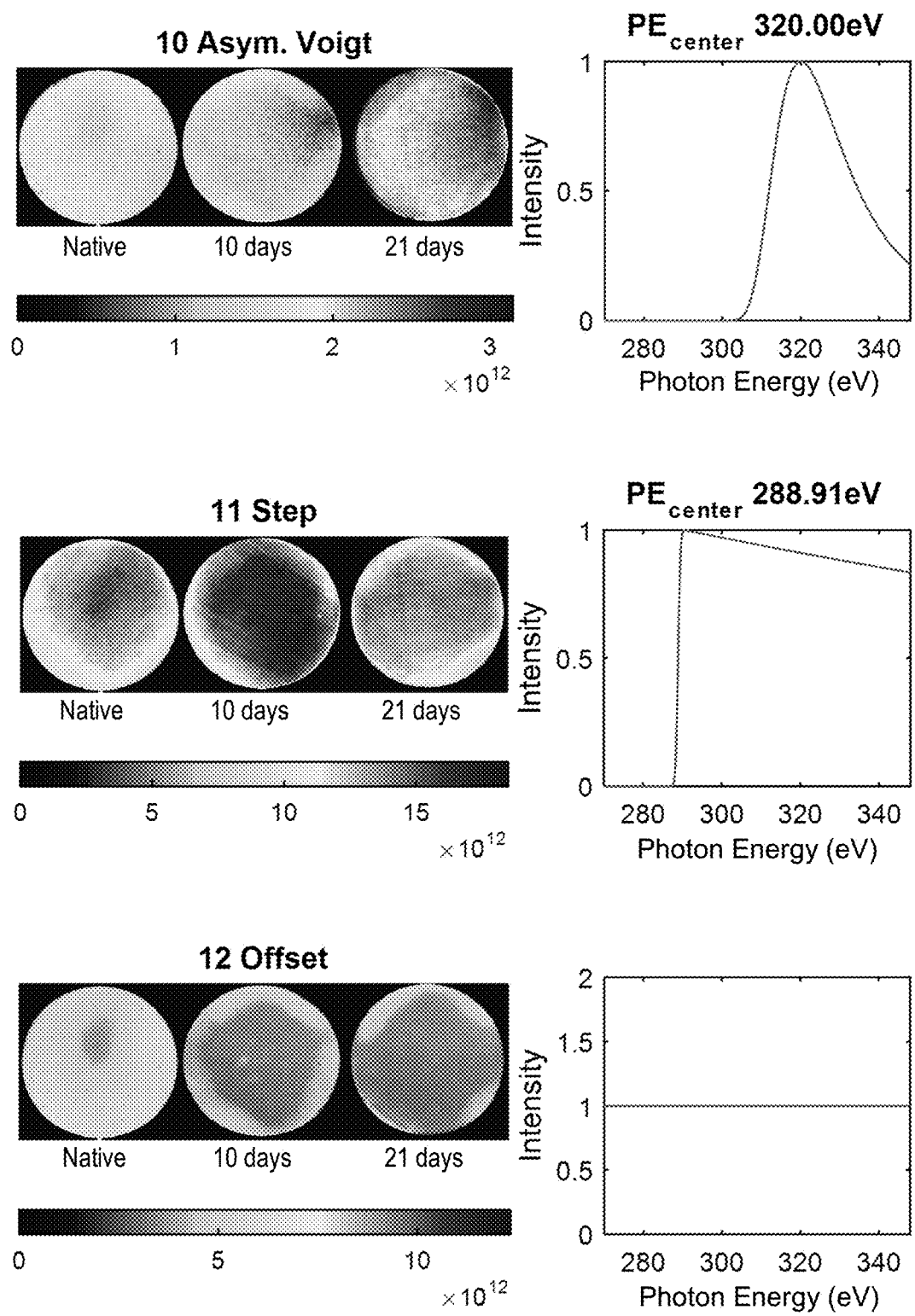

Using the analysis routine described herein, a mean spectrum was analyzed. This analysis provided a reconstructed spectrum (FIG. 12A, dashed lines) that accurately represented the obtained spectrum (FIG. 12A, solid black line). The reconstructed spectrum is composed of 12 different factors (labeled 1 to 12 in FIG. 12A), and general assignments from contributions from C—H, C—C, or C=C orbitals are provided in FIG. 12B. As seen in FIG. 12B, the polymer includes a polybutadiene portion and a polyacrylonitrile portion. Typically, an NEXAFS spectrum of solely polybutadiene exhibits a strong peak centered at 285.14 eV attributed to a C1s (C—H)→$\pi^*_{C=C}$ transition with other minor peaks (see, e.g., Dhez O et al., "*J. Electron Spectrosc. Relat. Phenom.* 2003; 128(1):85-96). In contrast, the spectrum in FIG. 12B shows a strong peak centered around 284 eV and an even stronger peak (or peaks) centered around 288 eV. The peak(s) around 288 eV likely include contribution by the $\pi^*$ orbitals of the nitrile CN group, as observed in polyacrylonitrile having a single main peak centered at 286.58 eV. As can be seen, further analysis and bonding assignments can be facilitated by factor analysis.

We further wished to understand how each factor was affected by aging. Polymer aging is an area of active research, and understanding how and why particular bonds or chemical attributes change over use in the field can be helpful in developing new polymers and in assessing the lifetime of a polymeric article. FIG. 13A-13D shows the results of global analysis of the 12 factors, as well as the change in the contribution of each factor as the polymer was aged. In particular, factors 1 and 2 were further analyzed to understand their contribution to the NEXAFS spectrum upon aging. The contribution of factor 1 increased upon aging (FIG. 14A), whereas the contribution of factor 2 decreased upon aging (FIG. 14B). In addition, for the native sample, factor 2 dominated the spectrum over factor 1. Factors 1 and 2 are understood to arise from C1s (C—H) →$\pi^*_{C=C}$ contributions, and thermal aging can contribute to complicated C=C bonding interactions. Thus, further studies and global analysis can inform mechanistic understanding of complex aging phenomena driven by thermal or photo-induced damage.

Although the present application focused on analysis of single images, this method can be applied to multiple images and spectra by providing a data matrix encompassing such multidimensional data. In particular, the methods herein show promise for identifying variation in the spatial domain to aid in data interpretation, where such image inhomogeneities can be the result of interesting dynamic chemical phenomena.

Example 2: Global Analysis of NEXAFS Images of PTFE Samples

Figure 15B:
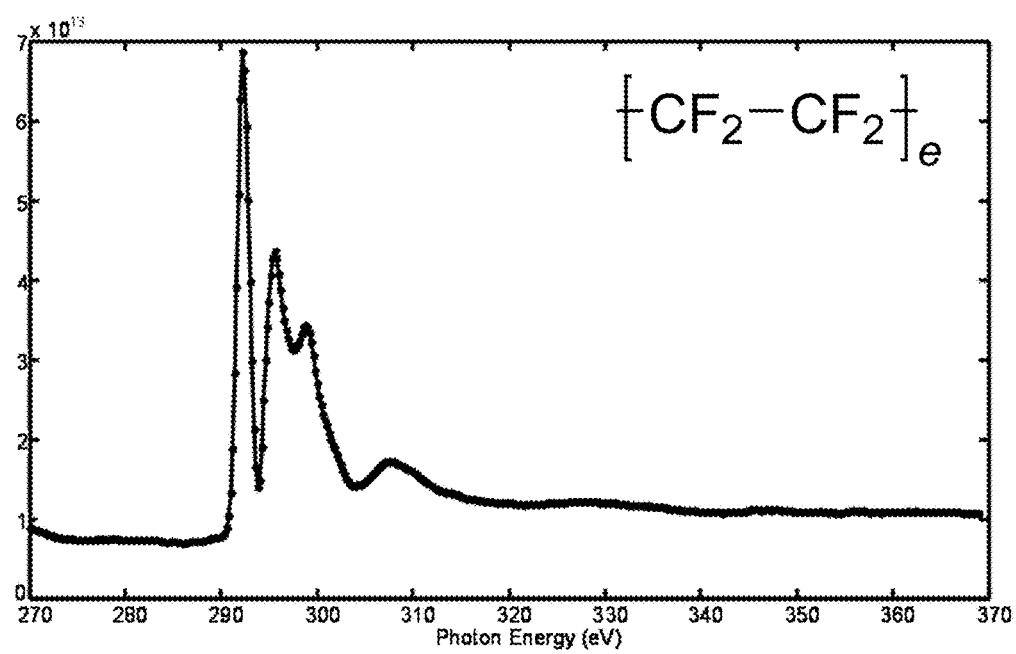
Figure 17:
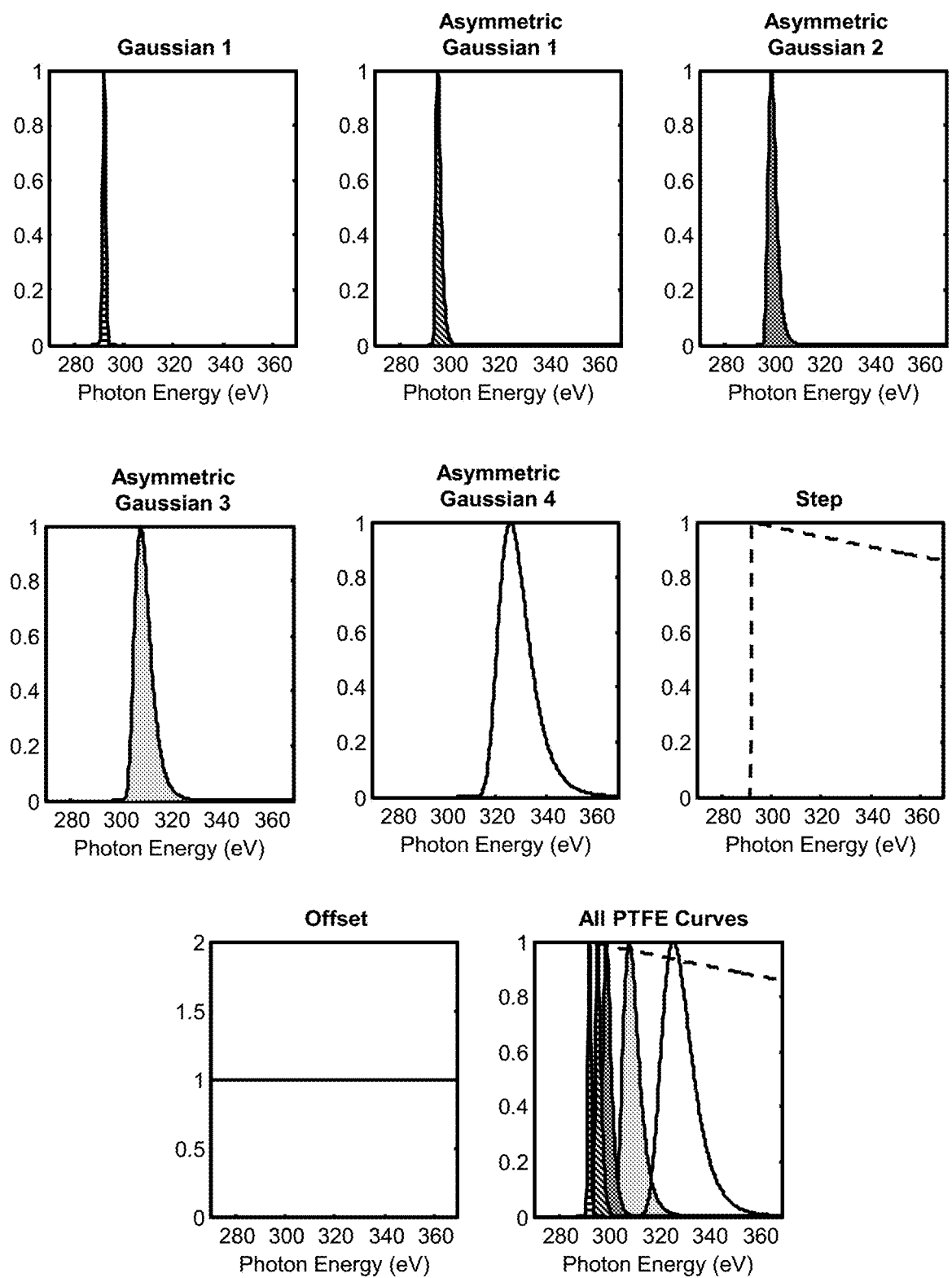
FIG. 17 shows reconstructed spectra of the 7 factors used to characterize the PTFE sample, as shown in FIG. 16, as well as a spectrum showing all 7 factors (labeled "All PTFE Curves").

Any useful sample can be analyzed with the processes herein. In addition to the nitrile sample, polytetrafluoroethylene (PTFE) samples were analyzed using NEXAFS and global analysis of the NEXAFS images. Provided is a spectrally summed PTFE image (FIG. 15A, left) and a region of interest within that image (FIG. 15A, right), as well as a mean spectrum (FIG. 15B) having identifiable peaks typically contributed to PTFE, e.g., a peak centered about 292 eV attributed to a C—F $\sigma^*$ absorption, a peak at about 296 eV for a C—C $\sigma^*$ absorption, and a peak at about 299 eV for another C—F $\sigma^*$ absorption (see, e.g., Gamble L J et al., "Surface structure and orientation of PTFE films determined by experimental and FEFF8-calculated NEXAFS spectra," *Langmuir* 2002; 18:2183-9). Each factor can be represented graphically (FIG. 16) or spectrally (FIG. 17).

Thus, the methods herein can be used to analyze various types of chemical sample exhibiting different spectral features.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method for analyzing a chemical test sample, the method comprising:
   (i) applying a thermal or photo-induced aging process to a chemical test sample, thereby producing an aged chemical test sample, wherein the aged chemical test sample is the polymer comprising nitrile or polytetrafluoroethylene;
   (ii) irradiating the aged chemical test sample;
   (iii) obtaining an image array of the aged chemical test sample after irradiation;
   (iv) employing a computer-implemented method to analyze the image array, wherein the computer-implemented method comprises:
   (a) receiving, with a processor, the image array of the aged chemical test sample after irradiation, wherein the array comprises $d_n$ number of emission images for each $n^{th}$ energy level, and wherein each image comprises dimensions of a by b, and wherein each of $d_n$, n, a, and b is, independently, an integer of 1 or more;
   (b) generating, with a processor, a data matrix D based on the image array, wherein D has a dimension of m by n, and wherein m is a times b;
   (c) performing, with a processor, global analysis of D, thereby generating a matrix A comprising linear terms and a matrix S comprising non-linear terms, wherein $D=AS^T$, A has a dimension of m by q, S has a dimension of n by q, and q is an integer of 1 or more that represents a number of factors,
   wherein generating the matrix A and the matrix S comprises initially non-linearly solving the non-linear terms in S and then linearly solving separately for the linear terms in A, and
   wherein each of q factors is characterized by a mathematical function that describes a spectral feature of a representation of the matrix D, and
   wherein q is less than n, and
   wherein the one or more factors are selected from the group consisting of a Gaussian function, a Lorentzian function, a pseudo-Voigt function, an asymmetric peak function, a shaped step function, and an offset function; and
   (d) converting the matrix A and the matrix S into one or more chemical spectra comprising q number of spectral features that characterizes the aged chemical test sample, thereby identifying one or more chemical bonds, atoms, or charges present in the aged chemical test sample; and
   (v) analyzing the one or more factors present in the aged chemical test sample, as compared to a native chemical sample, thereby characterizing an age of the aged chemical test sample.

2. The method of claim 1, wherein step (c) comprises a non-negativity constraint.

3. The method of claim 1, wherein step (c) comprises:
   (c4) solving for an estimated matrix $\hat{S}$ by non-linearly solving D=AST, wherein the estimated matrix $\hat{S}$ is an estimate of S;
   (c5) solving for an estimated matrix $\hat{A}$ using the estimated matrix $\hat{S}$ as S in the following equation $D=AS^T$, wherein the estimated matrix $\hat{A}$ is an estimate of A;
   (c6) computing a convergence metric; and
   (c7) iterating steps (c4) to (c6) until the convergence metric meets a convergence criterion.

4. The method of claim 3, further comprising:
   (c4') constructing an initial matrix $\hat{S}_{initial}$ composed of expected non-linear terms, wherein (c4') is conducted prior to step (c4).

5. The method of claim 4, wherein step (c4) comprises solving for an estimated matrix $\hat{S}$ by non-linearly solving $D=AS^T$ by beginning from the initial matrix $\hat{S}_{initial}$.

6. The method of claim 1, wherein step (c) comprises:
   (c8) constructing an initial matrix $\hat{S}_{initial}$ from expected non-linear terms;
   (c9) solving for an estimated matrix $\hat{S}$ by non-linearly solving $D=AS^T$ by beginning from the initial matrix $\hat{S}_{initial}$, wherein the estimated matrix $\hat{S}$ is an estimate of S;
   (c10) solving for an estimated matrix $\hat{A}$ using the estimated matrix $\hat{S}$ as S in the following equation $D=AS^T$, wherein the estimated matrix $\hat{A}$ is an estimate of A;
   (c11) computing a convergence metric; and
   (c12) iterating steps (c9) to (c11) until the convergence metric meets a convergence criterion.

7. The method of claim 1, wherein step (c) comprises:
   (c13) constructing an initial matrix $\hat{S}_{initial}$ from expected non-linear terms;
   (c14) solving for an estimated matrix $\hat{A}$ using the initial matrix $\hat{S}_{initial}$ as S in the following equation $D=AS^T$, wherein the estimated matrix $\hat{A}$ is an estimate of A;
   (c15) computing a convergence metric;
   (c16) if not converged, solving for an estimated matrix $\hat{S}$ by non-linearly solving $D=AS^T$, wherein the estimated matrix $\hat{S}$ is an estimate of S,
   (c17) iterating steps (c14) to (c16) until the convergence metric meets a convergence criterion.

8. The method of claim 1, wherein step (c) comprises applying a least squares minimization criterion to generate the matrix A and the matrix S.

9. The method of claim 1, further comprising:
   (c') compressing the data matrix D to provide a score matrix T and a loading matrix P, wherein $D=TP^T$ and (c') is conducted prior to (c).

10. The method of claim 9, wherein step (c) comprises performing, with a processor, global analysis of compressed D, thereby generating a matrix A comprising linear terms and a matrix S comprising non-linear terms, wherein $D=TP^T=AS^T$.

11. The method of claim 1, wherein one or more factors comprise a plurality of pseudo-Voigt functions.

12. The method of claim 1, wherein the image array comprises one or more absorption images or spectra of the aged chemical test sample.

13. The method of claim 12, wherein the absorption images or spectra comprise one or more X-ray absorption spectra, near edge X-ray absorption fine structure spectra, fluorescence spectra, infrared spectra, photon emission spectra, or photon absorption spectra.

14. A method for analyzing a chemical test sample, the method comprising:
  (i) applying a thermal or photo-induced aging process to a chemical test sample, thereby producing an aged chemical test sample, wherein the aged chemical test sample is the polymer comprising nitrile or polytetrafluoroethylene;
  (ii) irradiating the aged chemical test sample;
  (iii) obtaining an image array of the aged chemical test sample after irradiation;
  (iv) employing a computer-implemented method to analyze the image array, wherein the computer-implemented method comprises:
    (a) receiving, with a processor, the image array of the aged chemical test sample after irradiation, wherein the array comprises $d_n$ number of emission images for each $n^{th}$ energy level, and wherein each image comprises dimensions of a by b, and wherein each of $d_n$, n, a, and b is, independently, an integer of 1 or more;
    (b) generating, with a processor, a data matrix D based on the image array, wherein D has a dimension of m by n, and wherein m is a times b;
    (c) compressing the data matrix D to provide a score matrix T and a loading matrix P, wherein $D=TP^T$;
    (d) performing, with a processor, global analysis of D, thereby generating a matrix A comprising linear terms and a matrix S comprising non-linear terms, wherein $D=TP^T=AS^T$, A has a dimension of m by q, S has a dimension of n by q, and q is an integer of 1 or more that represents a number of factors,
      wherein generating the matrix A and the matrix S comprises initially non-linearly solving the non-linear terms in S and then linearly solving separately for the linear terms in A, and
      wherein each of q factors is characterized by a mathematical function that describes a spectral feature of a representation of the matrix D, and
      wherein q is less than n, and
      wherein the one or more factors are selected from the group consisting of a Gaussian function, a Lorentzian function, a pseudo-Voigt function, an asymmetric peak function, a shaped step function, and an offset function; and
    (e) converting the matrix A and the matrix S into one or more chemical spectra comprising q number of spectral features that characterizes the aged chemical test sample, thereby identifying one or more chemical bonds, atoms, or charges present in the aged chemical test sample; and
  (v) analyzing the one or more factors present in the aged chemical test sample, as compared to a native chemical sample, thereby characterizing an age of the aged chemical test sample.

15. The method of claim 14, wherein step (c) comprises an eigenanalysis of $D=TP^T$.

16. The method of claim 14, wherein step (c) comprises solving for the loading matrix P by analysis of $D=TP^T$.

17. The method of claim 14, wherein step (c) comprises:
  (c1) solving for the loading matrix P by analysis of $D=TP^T$; and
  (c2) solving for the score matrix T by using the loading matrix P.

18. The method of claim 17, wherein step (d) comprises:
  (d1) performing, with a processor, global analysis of D, thereby generating a first matrix $A_1$ comprising linear terms and a first matrix $S_1$ comprising non-linear terms;
  (d2) computing a first residual matrix $R_1$ that characterizes error between D and generated matrix $A_1$ and matrix $S_1$;
  (d3) iterating steps (d1) and (d2) until convergence to provide matrix A and matrix S for step (e).

19. The method of claim 17, wherein step (d) comprises:
  (d4) solving for an estimated matrix $\hat{S}$ by non-linearly solving $D=AS^T$, wherein the estimated matrix $\hat{S}$ is an estimate of S;
  (d5) solving for an estimated matrix $\hat{A}$ using the estimated matrix $\hat{S}$ as S, the matrix P, and the matrix T in the following equation $AS^T=TP^T$, wherein the estimated matrix $\hat{A}$ is an estimate of A;
  (d6) computing a convergence metric; and
  (d7) iterating steps (d4) to (d6) until the convergence metric meets a convergence criterion.

20. The method of claim 19, wherein step (d) comprises:
  (d12) computing the matrix A by using the estimator matrix $\tilde{A}$ in the following equation $A=T\tilde{A}$, wherein $T=DP$ and (d12) is conducted after (d11).

21. The method of claim 17, wherein step (d) comprises:
  (d8) solving for an estimated matrix $\hat{S}$ by non-linearly solving $D=AS^T$, wherein the estimated matrix $\hat{S}$ is an estimate of S;
  (d9) solving for an estimator matrix $\tilde{A}$ using the estimated matrix $\hat{S}$ as S and the matrix P in the following equation $P^T=\tilde{A}S^T$, wherein the estimator matrix $\tilde{A}$ is an estimator of A such that $A=T\tilde{A}$;
  (d10) computing a convergence metric; and
  (d11) iterating steps (d8) to (d10) until the convergence metric meets a convergence criterion.

22. The method of claim 17, wherein step (d) comprises applying a least squares minimization criterion to generate the matrix A and the matrix S.

23. The method of claim 22, wherein the absorption images or spectra comprise one or more X-ray absorption spectra, near edge X-ray absorption fine structure spectra, fluorescence spectra, infrared spectra, photon emission spectra, or photon absorption spectra.

24. The method of claim 14, wherein D is an m×n matrix, T is an m×p matrix, and $P^T$ is a p×n matrix; each of m, n, and p is an integer of 1 or more; and p is less than both m and n.

25. The method of claim 14, wherein step (d) comprises a non-negativity constraint.

26. The method of claim 14, wherein the image array comprises one or more absorption images or spectra of the aged chemical test sample.

* * * * *